United States Patent
Piskun et al.

(10) Patent No.: US 11,406,256 B2
(45) Date of Patent: *Aug. 9, 2022

(54) MULTI-LUMEN-CATHETER SYSTEM FOR A MINIMALLY-INVASIVE TREATMENT

(71) Applicant: Boston Scientific Scimed, Inc., Maple Grove, MN (US)

(72) Inventors: Gregory Piskun, Delray Beach, FL (US); John To, Newark, CA (US); Brian Tang, Fremont, CA (US); Mariel Fabro, San Francisco, CA (US); Oleg Shikhman, Trumbull, CT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 334 days.

This patent is subject to a terminal disclaimer.

(21) Appl. No.: 16/779,784

(22) Filed: Feb. 3, 2020

(65) Prior Publication Data
US 2020/0170499 A1    Jun. 4, 2020

Related U.S. Application Data

(63) Continuation of application No. 15/331,858, filed on Oct. 22, 2016, now Pat. No. 10,588,504, which is a
(Continued)

(51) Int. Cl.
*A61B 1/32* (2006.01)
*A61B 17/02* (2006.01)
(Continued)

(52) U.S. Cl.
CPC ............ *A61B 1/32* (2013.01); *A61B 1/00082* (2013.01); *A61B 1/00085* (2013.01);
(Continued)

(58) Field of Classification Search
CPC ....... A61B 1/32; A61B 17/02; A61B 17/0218; A61B 17/0206; A61M 39/22; A61M 39/32; A61M 13/00
See application file for complete search history.

(56) References Cited

U.S. PATENT DOCUMENTS

| 827,193 A | 7/1906 | Thrash |
| 2,072,346 A | 3/1937 | Smith |

(Continued)

FOREIGN PATENT DOCUMENTS

| CN | 1579352 A | 2/2005 |
| CN | 101048101 A | 10/2007 |

(Continued)

OTHER PUBLICATIONS

*Oleg Shikhman* v. *Bobcat Endscopy LLC, et al.*, Memorandum of Decision, filed Oct. 31, 2019, 22 pages. (p. 1, line 15—p. 2, line 3; p. 2, lines 7-8, p. 7, lines 4-6; p. 8, lines 3-13; p. 10, line 4—p. 11, line 9; p. 18, line 5—p. 19, line 2; p. 18. footnote 15.).
(Continued)

*Primary Examiner* — Christopher J Beccia
(74) *Attorney, Agent, or Firm* — Seager, Tufte & Wickhem LLP

(57) ABSTRACT

A system for performing minimally invasive procedures in a body lumen of a patient including a flexible catheter having a first lumen configured and dimensioned to receive an endoscope therethrough and a second lumen configured and dimensioned to receive a first flexible tube therethrough. The first flexible tube is movable through the second lumen and has a distal portion including a first curve extending in a first direction with respect to the longitudinal axis and a second curve extending in a second different direction with respect to the longitudinal axis. A retractor system is positioned at a distal portion of the catheter and is movable from a non-expanded insertion position to an expanded position
(Continued)

forming an expanded cage to form a larger working space. The distal portion of the first flexible tube is movable within the expanded cage.

20 Claims, 29 Drawing Sheets

Related U.S. Application Data continuation of application No. 14/099,943, filed on Dec. 7, 2013, now Pat. No. 9,565,998, which is a continuation-in-part of application No. 13/726,147, filed on Dec. 23, 2012, now Pat. No. 9,161,746, which is a continuation of application No. 12/970,604, filed on Dec. 16, 2010, now Pat. No. 8,506,479, said application No. 14/099,943 is a continuation-in-part of application No. 13/913,466, filed on Jun. 9, 2013, now Pat. No. 9,186,131, which is a continuation-in-part of application No. 12/970,604, filed on Dec. 16, 2010, now Pat. No. 8,506,479, said application No. 13/913,466 is a continuation-in-part of application No. 13/531,477, filed on Jun. 22, 2012, now Pat. No. 8,932,211.

(60) Provisional application No. 61/287,077, filed on Dec. 16, 2009.

(51) Int. Cl.
*A61B 1/00* (2006.01)
*A61B 1/018* (2006.01)
*A61B 1/31* (2006.01)
*A61B 17/00* (2006.01)
*A61M 13/00* (2006.01)
*A61M 39/22* (2006.01)
*A61B 1/015* (2006.01)
*A61B 17/34* (2006.01)
*A61B 17/04* (2006.01)
*A61B 18/04* (2006.01)
*A61B 18/00* (2006.01)

(52) U.S. Cl.
CPC ...... *A61B 1/00087* (2013.01); *A61B 1/00128* (2013.01); *A61B 1/00154* (2013.01); *A61B 1/015* (2013.01); *A61B 1/018* (2013.01); *A61B 1/31* (2013.01); *A61B 17/00234* (2013.01); *A61B 17/0206* (2013.01); *A61B 17/0218* (2013.01); *A61M 13/00* (2013.01); *A61M 39/22* (2013.01); *A61B 17/0469* (2013.01); *A61B 18/04* (2013.01); *A61B 2017/0034* (2013.01); *A61B 2017/00269* (2013.01); *A61B 2017/00331* (2013.01); *A61B 2017/00353* (2013.01); *A61B 2017/00464* (2013.01); *A61B 2017/00477* (2013.01); *A61B 2017/00557* (2013.01); *A61B 2017/00818* (2013.01); *A61B 2017/00867* (2013.01); *A61B 2017/0225* (2013.01); *A61B 2017/345* (2013.01); *A61B 2017/3445* (2013.01); *A61B 2018/00601* (2013.01)

(56) References Cited

U.S. PATENT DOCUMENTS

| | | |
|---|---|---|
| 3,495,586 A | 2/1970 | Eberhard |
| 3,557,794 A | 1/1971 | Van Patten |
| 4,718,406 A | 1/1988 | Bregman et al. |
| 5,840,031 A | 11/1998 | Crowley |
| 5,954,731 A * | 9/1999 | Yoon ............... A61B 17/062 606/147 |
| 6,443,959 B1 | 9/2002 | Beland et al. |
| 6,605,078 B2 | 8/2003 | Adams |
| 7,063,659 B2 | 6/2006 | Goto et al. |
| 9,039,601 B2 | 5/2015 | Piskun |
| 9,050,004 B2 * | 6/2015 | Diao ............... A61B 1/04 |
| 10,588,504 B2 * | 3/2020 | Piskun ............. A61B 1/32 |
| 2001/0056260 A1 | 12/2001 | Grimes et al. |
| 2003/0187494 A1 | 10/2003 | Loaldi |
| 2004/0210116 A1 | 10/2004 | Nakao |
| 2005/0251177 A1 * | 11/2005 | Saadat ............ A61B 17/0401 606/153 |
| 2005/0273085 A1 | 12/2005 | Hinman et al. |
| 2006/0189845 A1 * | 8/2006 | Maahs ............. A61B 1/018 600/146 |
| 2008/0058590 A1 | 3/2008 | Saadat et al. |
| 2008/0262492 A1 | 10/2008 | Lee |
| 2009/0149716 A1 * | 6/2009 | Diao ............... A61B 17/0218 600/207 |
| 2010/0094327 A1 | 4/2010 | Milsom et al. |
| 2012/0053485 A1 | 3/2012 | Bloom |
| 2014/0142393 A1 | 5/2014 | Piskun et al. |
| 2015/0327754 A1 | 11/2015 | Leeflang et al. |

FOREIGN PATENT DOCUMENTS

| | | |
|---|---|---|
| CN | 100452044 C | 1/2009 |
| CN | 100462044 C | 2/2009 |
| CN | 103340679 A | 10/2013 |
| CN | 104135972 A | 11/2014 |
| JP | H06296617 A | 10/1994 |
| JP | H09503677 A | 4/1997 |
| JP | 2001527429 A | 12/2001 |
| JP | 2003033436 A | 2/2003 |
| JP | 2003522590 A | 7/2003 |
| JP | 2004154485 A | 6/2004 |
| JP | 2011072782 A | 4/2011 |
| JP | 2015000280 A | 1/2015 |
| JP | 2016526397 A | 9/2016 |
| WO | 2014164661 A1 | 10/2014 |

OTHER PUBLICATIONS

Extended European Search Report and Written Opinion for the European Patent Application No. EP19214866, dated Apr. 20, 2020, 10 pages.

International Search Report and Written Opinion for the International Patent Application No. PCT/US2020/063710, dated Mar. 30, 2021, 15 pages.

European Search Report for the European Patent Application No. EP19214960, dated Apr. 17, 2020, 6 pages.

European Search Report for the European Patent Application No. EP20151480, dated Jul. 10, 2020, 9 pages.

\* cited by examiner

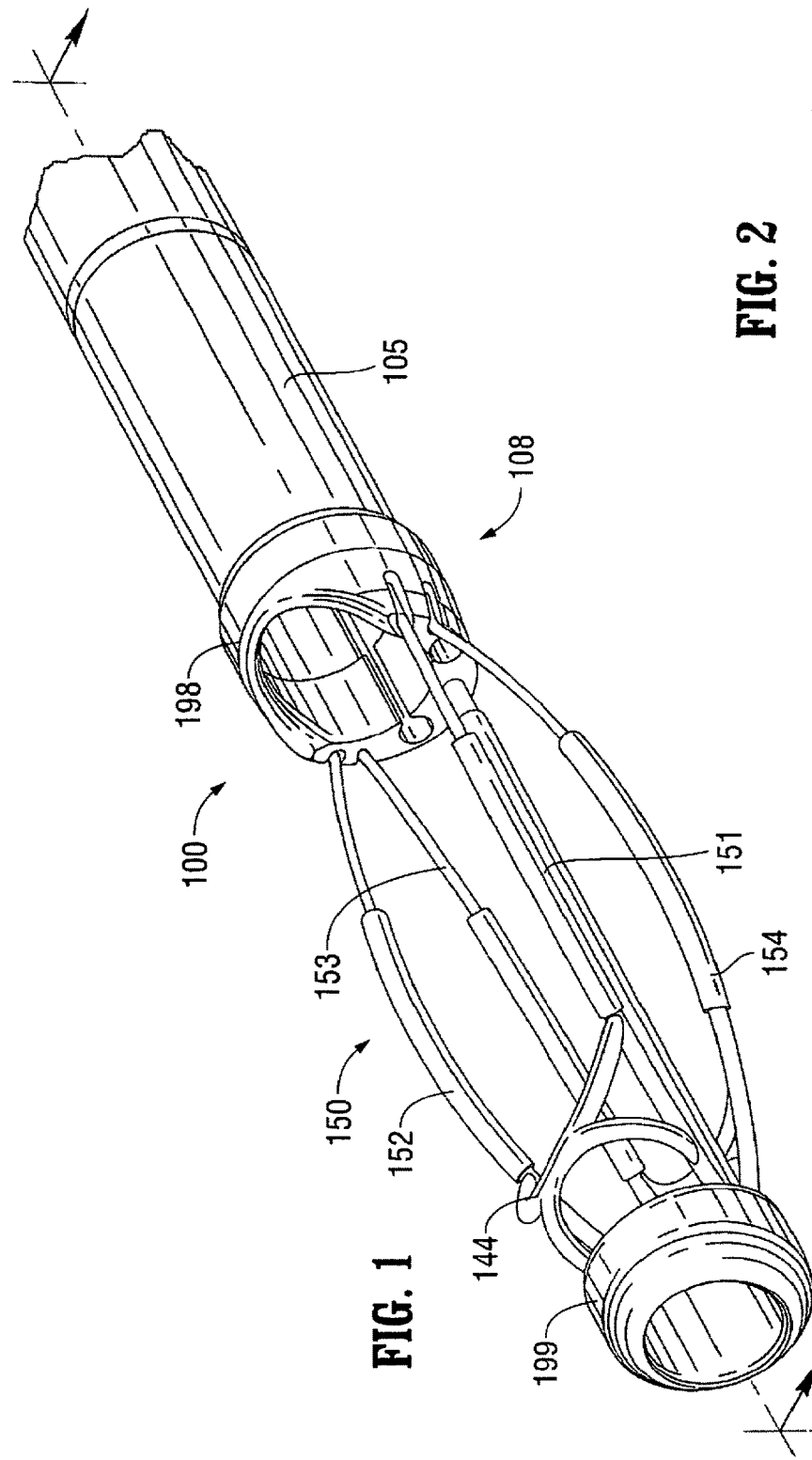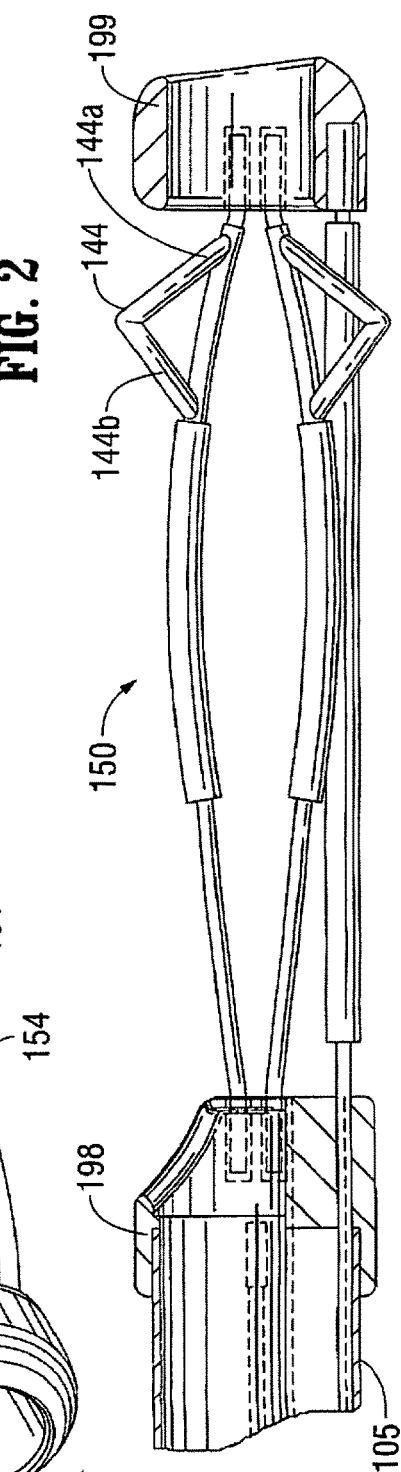

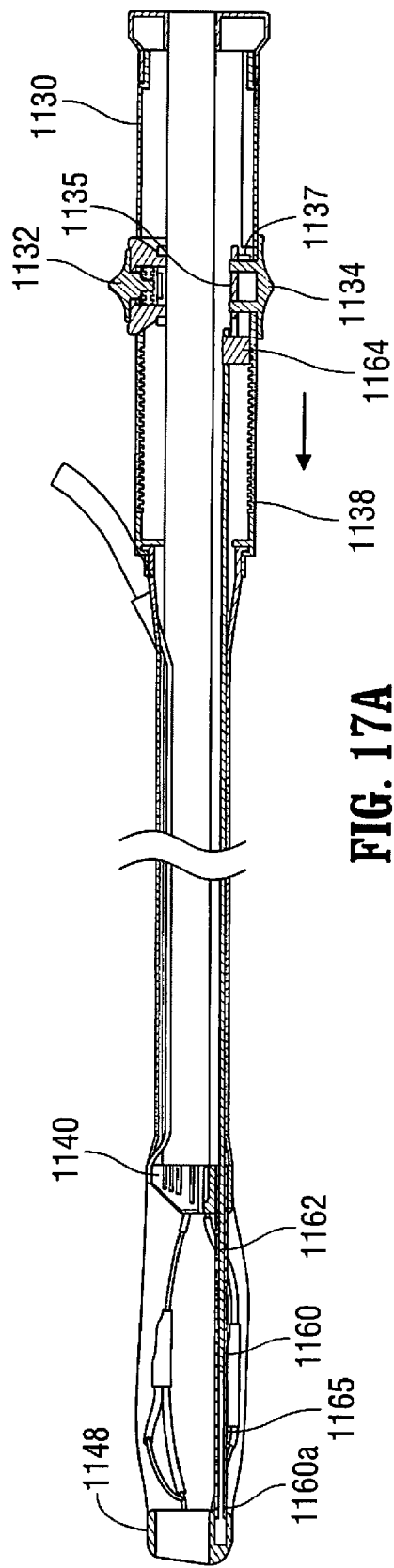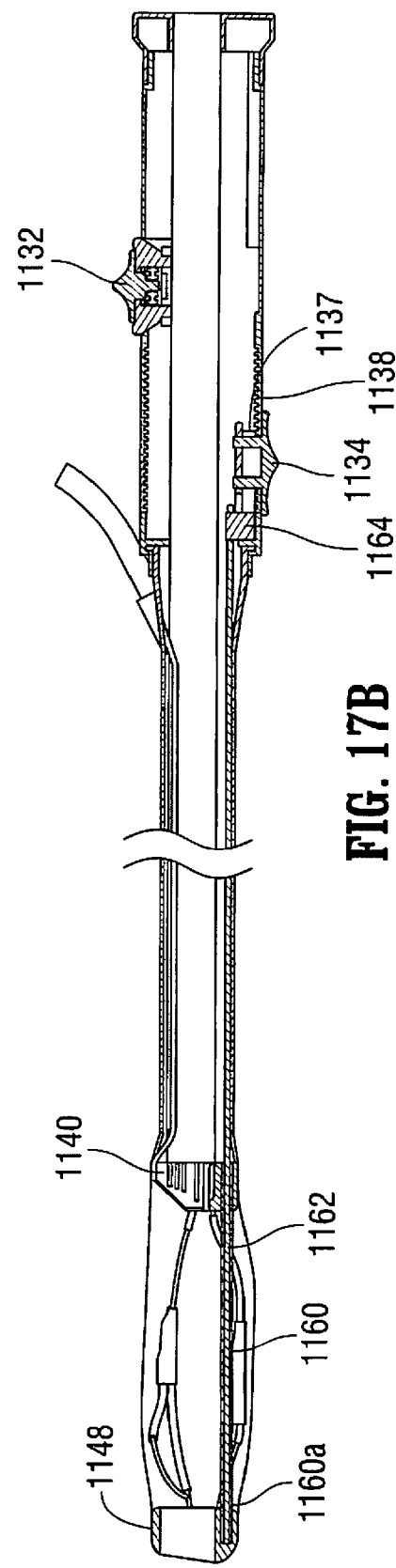
FIG. 17A
FIG. 17B

MULTI-LUMEN-CATHETER SYSTEM FOR A MINIMALLY-INVASIVE TREATMENT

CROSS-REFERENCE TO RELATED APPLICATIONS

This application is a continuation of U.S. application Ser. No. 15/331,858, filed on Oct. 22, 2016, which is a continuation of U.S. application Ser. No. 14/099,943, filed Dec. 7, 2013, now U.S. Pat. No. 9,565,998, which is a continuation in part of U.S. application Ser. No. 13/726,147, filed Dec. 23, 2012, now U.S. Pat. No. 9,161,746, which is a continuation of U.S. application Ser. No. 12/970,604, filed Dec. 16, 2010, now U.S. Pat. No. 8,506,479, which claims priority under 35 U.S.C. § 119 to U.S. Provisional Application Ser. No. 61/287,077, filed Dec. 16, 2009 and is a continuation-in-part of U.S. application Ser. No. 13/913,466, filed Jun. 9, 2013, now U.S. Pat. No. 9,186,131, which is a continuation-in-part of U.S. application Ser. No. 12/970,604, filed Dec. 16, 2010, now U.S. Pat. No. 8,506,479, which claims priority under 35 U.S.C. § 119 to U.S. Provisional Application Ser. No. 61/287,077, filed Dec. 16, 2009, and is a continuation-in-part of application U.S. application Ser. No. 13/531,477, filed Jun. 22, 2012, now U.S. Pat. No. 8,932,211. The entire contents of each of these applications are incorporated herein by reference.

BACKGROUND

Field of the Invention

The teachings provided herein are generally directed to improved methods and devices for operatively treating gastrointestinal disorders in a minimally-invasive manner.

Description of the Related Art

Endoscopic procedures involving the gastrointestinal system offer advantages over conventional surgery in that they are less invasive and may provide visualization. These procedures continue to evolve to address problems and provide new methods of treatment identified by those skilled in the art.

One current problem includes a lack of technology for an optimal minimally-invasive expansion of a working space adjacent to the target tissues that could otherwise collapse around the target lesion or defect during an operative treatment. Having the ability to effectively expand the working space could markedly facilitate an intra-luminal operation. An expanded working space allows the instruments and endoscope to be independently manipulated and properly visualized around the target tissue. One of skill would appreciate having the ability to see and approach both the target tissue and the surrounding anatomy for reference, orientation, and surgical maneuvering.

Another current problem includes a lack of an endoscopic technology for organizing the endoscope, instruments, and working space in a manner that can maximize the working space for the treatment. The larger working space can improve the ability to manipulate the instruments (and endoscope) in a minimally-invasive manner from outside the body. Namely, it would be desirable to have a working space that has a point of entry for the instruments that is as far as practical from the target tissue to provide additional flexibility in approaching and visualizing the target tissue, perhaps providing more operating room for selecting a trajectory of the instruments toward the target tissue that is, for example, at least substantially perpendicular to the plane of dissection of the target tissue. Having a technology to overcome this problem would provide the person of skill with a system and procedure that is more desirable for a removal of tissue.

In view of at least the above, one of skill in the art of endoscopic, gastrointestinal surgical treatments would appreciate the technology taught herein which provides (i) a minimally-invasive expansion of the intra-luminal working space; and (ii) an organization of the endoscope instruments, such as the retractor and tools to maximize the working space and maneuverability, allowing for a maximum flexibility in approaching and visualizing the target tissue. It should be appreciated that having such improvements would reduce the technical complexity, and increase the efficacy and safety of, otherwise complex endoscopic operations. Moreover, doing so at a low cost, while using an affordable system that is introduced in the subject atraumatically and in a manner that does not substantially disrupt the conventional colonoscopy workflow, would be seen by those of skill as a very substantial advancement in the field of endoscopic surgical procedures.

SUMMARY

The teachings provided herein are generally directed to improved methods and devices for operatively treating gastrointestinal disorders in a minimally-invasive manner. The systems, for example, can include an endoscopic surgical suite.

In one aspect of the present disclosure, a system for performing minimally invasive procedures in a body lumen of a patient, such as a gastrointestinal tract, is provided comprising a flexible catheter having a first lumen configured and dimensioned to receive an endoscope therethrough and a second lumen configured and dimensioned to receive a first flexible tube therethrough. The first flexible tube is movable through the second lumen and has a first channel (lumen) extending therethrough dimensioned and configured to receive a first endoscopic tool (instrument) for axial movement therein, the first flexible tube terminates in a distal opening and has a longitudinal axis and a distal portion movable to an angled (or curved) position with respect to the longitudinal axis. The distal portion includes a first curve extending in a first direction with respect to the longitudinal axis and a second curve extending in a different direction with respect to the longitudinal axis. A retractor system is positioned at a distal portion of the catheter, the retractor system including first and second flexible elements movable from a non-expanded insertion position to an expanded position forming an expanded cage to form a larger working space, the distal portion of the first flexible tube movable within the expanded cage wherein the first curve increases a distance to a target lesion from the distal opening of the first flexible tube. A covering can be provided for at least a portion of the retractor system, the covering having an opening to receive body tissue.

In some embodiments, the catheter has a third lumen configured and dimensioned to receive a second flexible tube, the second flexible tube having a second channel (lumen) extending therethrough configured and dimensioned to receive a second endoscopic tool (instrument) for axial movement therein. The second flexible tube can have a longitudinal axis and a distal portion movable to an angled (or curved) position with respect to the longitudinal axis. The distal portion includes a first curve extending in a first direction with respect to the longitudinal axis and a second curve extending in a different direction with respect to the longitudinal axis. The second flexible tube can be slidable axially within the third lumen and the distal portion of the second flexible tube can be movable within the expanded cage.

In some embodiments, the first flexible tube and/or second flexible tube are unattached to the catheter. In some embodiments, the distal tips of the flexible tubes can be substantially aligned with the longitudinal axis when positioned within the lumens of the catheter and return to the angled position when exposed from the second and third lumens.

In some embodiments, the cage further comprises third and fourth elements, wherein upon expansion of the retractor system to the expanded position the first, second, third and fourth elements move from their collapsed insertion position outwardly away from a longitudinal axis of the catheter to the expanded position.

The system in some embodiments can include a stabilizer movable from a first position to a second position to increase the stability and rigidity of the cage (retractor system). In some embodiments, the cage includes a fifth flexible element, and the stabilizer comprises a stabilizing element movable within a lumen of, or alternatively, over, the fifth element.

The system can include an actuator positioned at a proximal region of the catheter and operably coupled to the first and second flexible elements to move the first and second elements between the non-expanded and expanded positions.

In some embodiments, a retaining (locking) mechanism is provided to maintain the actuator in one of several positions to retain (lock) the first and second elements in a desired expanded position. A release mechanism can be provided for releasing the retaining mechanism.

The system in some embodiments includes a proximal coupler to retain a proximal portion of the first and second elements and a distal coupler to retain a distal portion of the first and second elements, wherein the proximal and distal couplers can include an opening dimensioned to receive the endoscope therethrough when the catheter is backloaded over the endoscope. In some embodiments, a distal portion of the covering is attached to the distal coupler and a proximal portion of the covering is attached to the proximal coupler.

The covering can be closable to encapsulate tissue therein for removal. A flexible closing member such as a suture can be attached to the covering, wherein the flexible closing member is pulled to close the covering.

In some embodiments, a first and/or second transverse bridge member can be provided. The first transverse bridge member can be provided to join the first and second flexible elements to increase the rigidity of the retractor system. The second transverse bridge member can be provided to join the third and fourth elements to increase the rigidity of the retractor system.

In accordance with another aspect of the present disclosure, a method for performing a minimally invasive procedure in a body lumen of a patient, such as a gastrointestinal tract, is provided. The method preferably comprises the steps of placing a flexible catheter over a proximal region of a flexible endoscope, inserting the flexible endoscope in the body lumen to visualize target tissue, advancing the catheter over the endoscope, expanding a retractor system from a non-expanded insertion position to an expanded position to expand the body lumen to create a larger working space, and maneuvering a first flexible tube within the catheter, the first flexible tube having a double curved tip and being axially movable and rotatable within the catheter to locate and orient the curved tip. The distal portion of the flexible tube includes a first curve extending in a first direction with respect to the longitudinal axis and a second curve extending in a different direction with respect to the longitudinal axis. The method preferably further comprises the step of maneuvering a first endoscopic instrument (tool) within the first flexible tube, wherein the first flexible tube can be located at a selected position to define a fixed second curve and the endoscopic tool can be movable axially to adjust a distance between a distal tip of the first endoscopic tool and target tissue without changing the selected position or curvature of the fixed second curve.

In some embodiments, the method can include the steps of a) maneuvering a second flexible tube within the catheter, the second flexible tube having a double curved tip (first and second curves extending in different directions) and being axially movable and rotatable within the catheter to locate and orient its distal curved tip; and b) maneuvering a second endoscopic tool within the second flexible tube, wherein the second flexible tube can be located at a selected position to define a fixed second curve and the second endoscopic tool can be movable axially to adjust a distance between a distal tip of the second endoscopic tool and the target tissue without changing the selected position or curvature of the fixed second curve.

In some embodiments, the distal tip of the first flexible tube and/or the distal tip of the second flexible tube is normally curved and is in a substantially straightened position when in the confines of the catheter during insertion and automatically assumes a curved position when exposed from the confines of the catheter.

In some embodiments, the first and second flexible tubes are independently axially movable and independently rotatable. In some embodiments, the flexible tubes are removably insertable through the catheter and remain unattached to the catheter.

In some embodiments, the first and second endoscopic tools are angled toward the target tissue to achieve triangulation with the target tissue.

The method can further include the step of inserting a working instrument through a working channel of the endoscope and into the working space created by the retractor system.

The retractor system can include a covering, and the method can further include the step of closing the covering to encapsulate target tissue for removal.

The method can further comprise the step of rigidifying the retractor. In some embodiments, a control is actuated to distally advance rigidifying structure with respect to the retractor system to rigidify and stabilize the retractor system.

The teachings in another aspect include a floating, multi-lumen-catheter retractor system for ease of positioning in a subject. In some embodiments, the systems comprise a highly flexible outer tube configured for guiding a floating channel and a floating endoscope in an at least substantially floating arrangement within the system. This flexible outer tube can have a lumen, a proximal end, and a distal end with a double curve. And, during a use of the system, the floating channel can serve as a guide through which a tool is manipulated in a treatment of a target tissue in a subject. In some embodiments, the tool can include a grasper, a forceps, a snare, a clamp, a scissor, a knife, a dissector, an endoscopic stapler, a tissue loop, a clip applier, a suture-delivering instrument, or an energy-based tissue coagulator or cutter.

And, in some embodiments, the floating channel can have an elevator component for moving a bendable section to manipulate the tool.

In the system utilizing a floating channel, the floating channel can be at least substantially attached to the lumen of the outer tube at a first proximal location and a first distal location, and be at least substantially floating in the lumen of the outer tube between the first proximal location and the first distal location. Likewise, during the use of such system, in some embodiments, the floating endoscope can be at least slidably-attached to the lumen of the outer tube at a second proximal location and a second distal location, and be at least substantially floating in the lumen of the outer tube between the second proximal location and second distal location. The floating arrangement can increase the flexibility of the system and facilitate positioning the system in the subject for the treatment of the target tissue.

The systems provided herein can be used in several different methods of treatment. For example, the systems can be used in a method of treating a gastrointestinal lesion using a multidirectional and multi-angular approach to the lesion. The method can include positioning the system in a subject's gastrointestinal tract, the positioning including placing the retractor in proximity to a target lesion for a treatment; expanding the retractor to create the treatment space for use of the tool; improving visualization, for example, some lesions can be seen much better when tissue is retracted and stabilized; optimally positioning the target tissue in relation to the tool, for example, by optimizing the position of the duodenal papilla, facilitating its cannulation during a procedure; treating the target tissue with the tool; collapsing the retractor; and, withdrawing the system from the subject. The lesion can include, for example, a perforation, a tissue pathology a polyp, a tumor, a bleed, a diverticuli, an ulcer, a cancerous tissue, an abnormal vessel, or an appendix.

BRIEF DESCRIPTION OF THE DRAWINGS

FIG. 1 is a perspective view of a first embodiment of a system for operatively treating gastrointestinal disorders in a minimally-invasive manner, the retractor system shown in the collapsed position.

FIG. 2 is a longitudinal cross-sectional view of the system of FIG. 1.

FIGS. 17A and 17B are side views in partial cross-section showing movement of the actuator from a proximal position to a distal position to advance the rigidifying structure to stiffen the retractor system.

DETAILED DESCRIPTION

Figure 3:
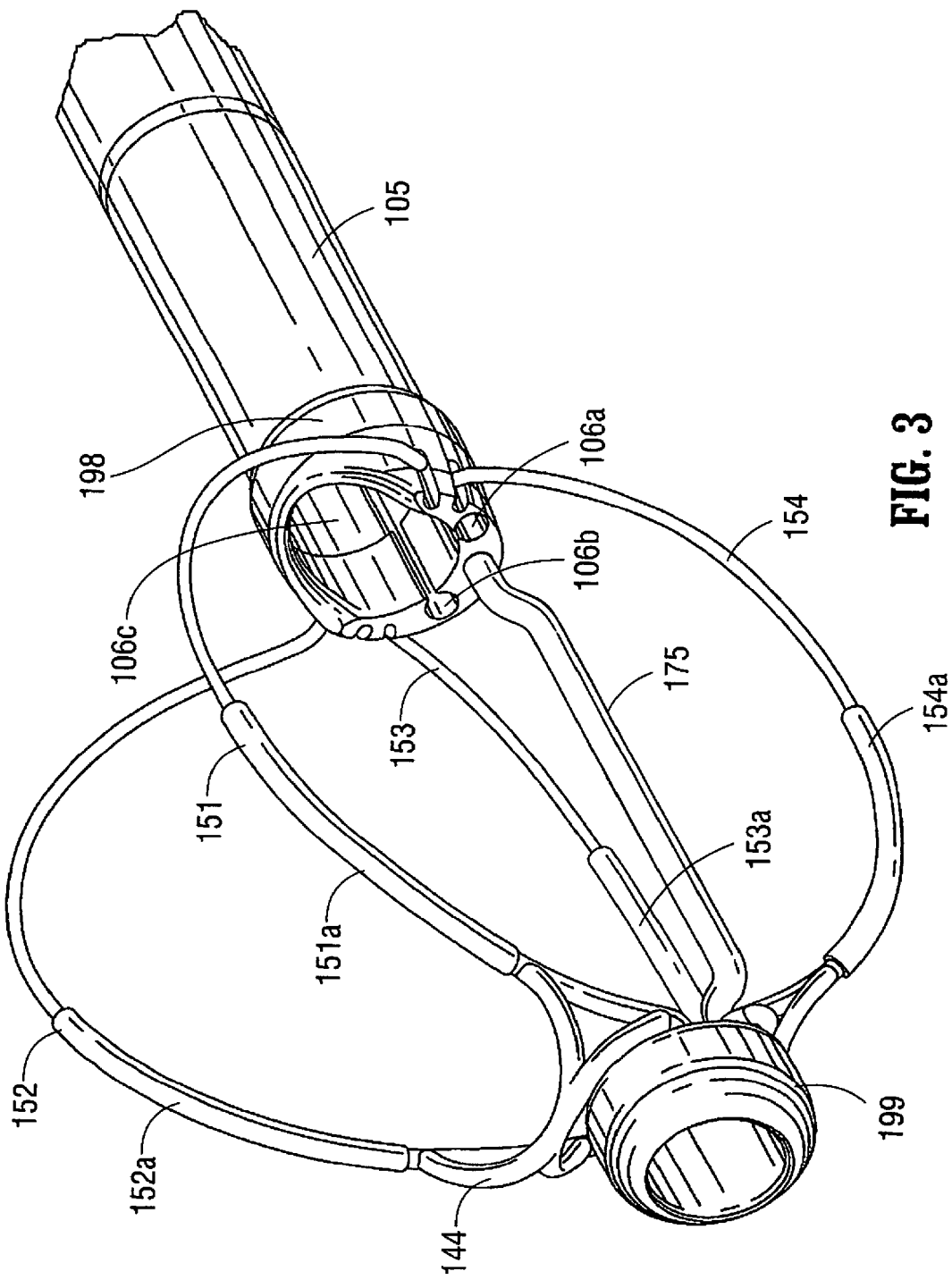
FIG. 3 is a perspective view similar to FIG. 1 illustrating the retractor system in the expanded position.

The teachings provided herein are generally directed to improved methods and devices for operatively treating gastrointestinal disorders endoscopically (in a minimally-invasive manner). The systems include an endoscopic surgical suite that is created by the systems disclosed herein. The surgical suite has a reversibly-expandable retractor that expands substantially symmetrically, and the tool channels have a double curved configuration described in detail below which maximize the distance from the tool to the target tissue to thereby maximize space for one or more tools and/or an endoscope to each be maneuvered independently to visualize a target tissue and treat the target tissue from outside the patient in a minimally invasive manner. Embodiments taught herein can provide, among other improvements, an increase in distance between tool ports and the target tissue to enhance the independent maneuverability and triangulation of each of the tools with respect to the target tissue. This increase in distance can also provide a way of obtaining a larger field of view. The systems taught herein, for example, can (i) enable a working space to be configured around the target tissue in tortuous body lumens and orifices such as the gastrointestinal tract using controls from outside the body; (ii) provide a flexible, passageway for multiple surgical tools and instruments, such as endoscope and graspers, to be passed from outside the body towards the target tissues; and (iii) organize and control the instruments such as the grasper in the working space from outside the body.

In some embodiments disclosed herein, the catheter is placed over an articulating endoscope by inserting the articulating endoscope through a channel of the catheter; in other embodiments the catheter is placed over a flexible endoscope by backloading the catheter over a flexible endoscope, such as a conventional colonoscope. Then the endoscope, e.g., colonoscope, is inserted to a position adjacent the target tissue and then the catheter is advanced further over the flexible endoscope so the retractor is next to the target tissue.

In some embodiments disclosed herein, the endoscopic working instruments (tools) for treating the target tissue are inserted directly through a respective lumen or channel of the multi-lumen catheter. In these embodiments where the instruments (tools) are inserted directly into the lumen or channel of the catheter, the working instruments can have a double curve at a distal end which can automatically assume the double curved position when exposed from the catheter so it curves away and then toward the target tissue, or alternatively, the working instruments can have a mechanism actively controlled by the user to articulate/angle the distal tip to obtain the first and/or second curve. In either case, the working instruments would have the double curved configuration to maximize space as described below. In other embodiments, instead of the endoscopic working instruments (tools) being inserted directly into the channel or lumen of the catheter, a flexible tube (instrument guide) is inserted through the lumen or channel of the catheter and acts as a guide for the instrument. That is, the flexible tube is first inserted into the lumen or channel of the catheter and then the endoscopic instrument is inserted through the respective flexible tube. The flexible tube has a double curve at a distal end which can automatically assume the double curved position when exposed from the catheter so it can curve away then toward the target tissue, or alternatively, the flexible tube can have a mechanism actively controlled by the user to articulate/angle the distal tip to obtain the first and/or second curve. In these embodiments utilizing the flexible tubes, the curving and maneuverability of the flexible tubes controls the positioning and orientation of the endoscopic instruments, and therefore the endoscopic instruments need not be provided with a pre-curved tip or articulating mechanisms.

The double curve wherein the distal end of the tubes curves downwardly away (as viewed in the orientation of FIG. 5) from the longitudinal axis of the tube and then upwardly toward and in some embodiments past the longitudinal axis increases the distance from the opening in the tube to the target lesion as compared to a flexible tube with a single curve curving from the longitudinal axis toward the target lesion. This enhances access and maneuverability of the working tools inserted through the tubes. The same advantages are obtained with working tools with a double curve as compared to a tool with a single curve.

The methods, devices, and systems taught herein can be used for minimally-invasive procedures which involves minimal access trauma and minimal collateral tissue damage during a surgical operation. Minimally-invasive surgery is desirable to reduce trauma to the patient, speed the healing process, reduce risk and, thus, reduce the length and expense of a hospital stay by minimizing or avoiding tissue damage, or risk of tissue damage.

The systems disclosed herein also enable triangulation to be achieved. Tissue triangulation, wherein the tissue is triangulated between two endoscopic instruments, enhances access and maneuverability.

Figure 5:
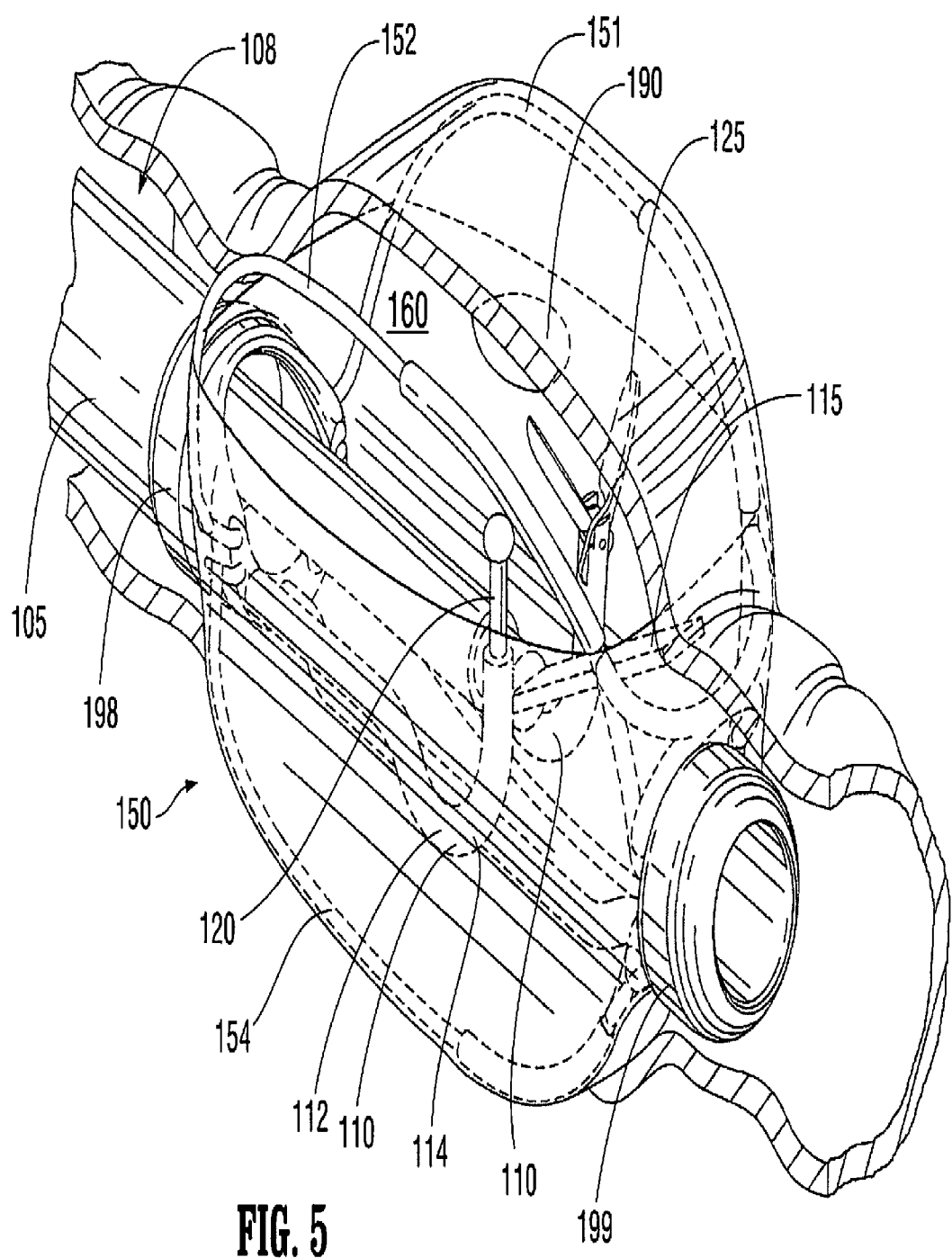
FIG. 5 illustrates the system of FIG. 1 being used to remove a lesion in a colon, the colon shown in a cutaway view to show the system in perspective, wherein the retractor system is in the expanded position, the tool channels extend from the catheter and the endoscopic tools extend from the tool channels.
Figure 6:
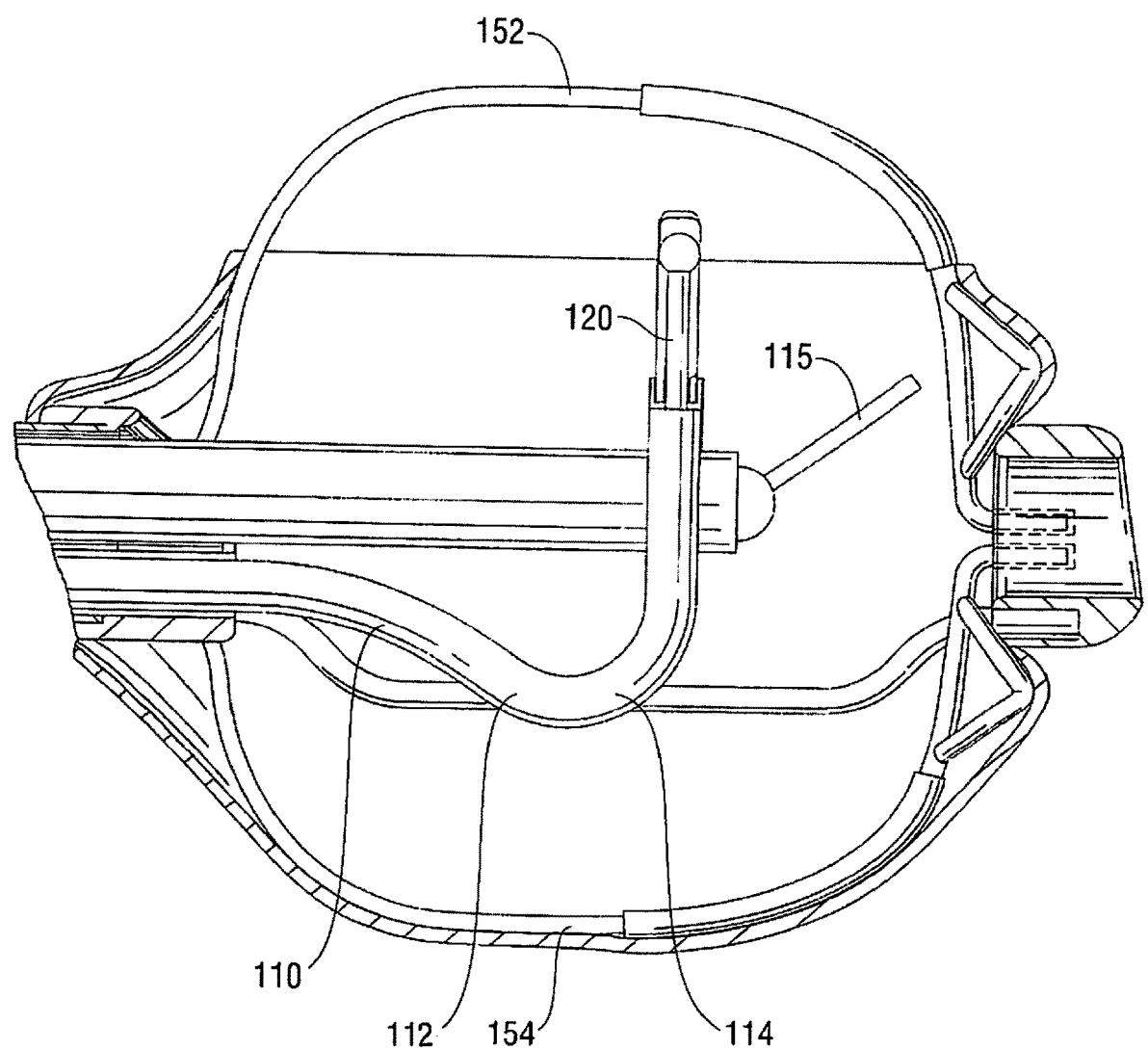
FIG. 6 is a side view of the system of FIG. 5.

FIGS. 1-7 illustrate one embodiment of a system for operatively treating gastrointestinal disorders endoscopically in and in a minimally-invasive manner. The system has a flexible outer tube 105 configured for guiding one or more channels 110 and an endoscope 115 within the system 100. The flexible outer tube 105 has a lumen, a proximal end (not shown), and a distal end 108 to house, for example, the channel(s) and the endoscope during use of the system 100. The lumen can extend from the proximal to the distal end so the tool channels 110 can be manipulated at a proximal end by the user. The outer tube 105 can alternatively be a multi-luminal tube, so a separate lumen accommodates the endoscope and the individual tool channels, and during the use of the system 100, the channel 110 can serve as a guide through which a tool 120, 125 can be inserted and manipulated in a treatment of a target tissue 190 in the gastrointestinal tract (or other areas) of the subject. The channel 110 can, for example, be in operable contact with an independently manipulable-and-articulable tool, and the channel can have an elevator component for moving a bendable section. Thus, the length of the channel in some embodiments is sufficient so it can extend out the proximal end of the outer tube 105 for manipulation by the user. The tool channels 110 are bendable or articulable at a distal end so they angle away from the longitudinal axis and then toward the target tissue 190. Such bendability can be achieved by providing tool channels (guides) 110 of shape memory material with a shape memorized bent position as shown in FIG. 5. When contained within the lumen of the outer tube 105 for insertion, the tool channels 110 would have a substantially straightened position, and when advanced from the distal end of the outer tube 105, would return to the double bent position of FIG. 5 having a first curve 112 and second curve 114. The first curve extends downwardly away from the longitudinal axis and the second curve extends upwardly towards the longitudinal axis. Clearly, if the system orientation changes, the designation "downwardly" and "upwardly" changes. The objective is to have the distal opening in the tool channels (and/or endoscopic instruments) face toward the target tissue, e.g., target lesion. In other embodiments, the tool channel 110 can have a mechanism such as an elevator component or a control wire attached to a distal end which can be pulled by the user or pulled by an actuator to move the tool channel to the double bent position. These different ways to achieve bendability of the tool channels can be used for the various embodiments of the systems described herein. The advantage of this double bent position is discussed below.

The tool inserted through the tool channel can be any tool known to one of skill. For example, the tool 120, 125 can include a grasper, a forceps, a snare, a scissor, a knife, a dissector, a clamp, an endoscopic stapler, a tissue loop, a clip applier, a suture-delivering instrument, or an energy-based tissue coagulator or cutter. The bendability of the channel 110 for moving a bendable section, often a distal end of the channel 110, manipulates, i.e., bends, the tool 120, 125 positioned therein. In some embodiments, at least one channel 110 and/or the endoscope 115 can have at least substantial freedom to move within the outer tube 105 during operation, or "float," such that the system 100 can be considered to be a floating, multi-lumen-catheter retractor system. It should be appreciated that the terms "tool" and "instrument" can be used interchangeably in some embodiments taught herein. As can be appreciated, the tool 120, 125 can be flexible, at least at a distal end such that when the tool channel 110 bends in a manner described herein, it also bends the tool which is positioned therein. Alternatively, it is also contemplated that the tool 120, 125 can be articulable or controllably bendable or composed of shape memory or other material so it bends without reliance on the bendability of the tool channels 110.

Although two tool channels 110 are illustrated, it should also be appreciated that a system with more than two tool channels or with only one tool channel can also be utilized. Additionally, the endoscope can have a working channel for insertion of a working instrument such as a grasper or dissector.

It is also contemplated that the tools can be provided with bendability characteristics so that they can be inserted directly through the lumen of the outer tube 105 without the need for tool channels. In these embodiments, the tools themselves have the bendable or articulable feature so as not to rely on the tool channels for achieving the double curve and bending/angling toward the target tissue.

The system includes a reversibly-expandable retractor 150, as shown in FIG. 1, that expands to form a treatment space or working chamber 160 in the subject. The retractor 150 can be configured, for example, for the expansion to occur distal to the distal end 108 of the outer tube 105. The retractor 150 can include retractor elements 151, 152, 153, 154, along with a proximal coupler 198 operably connected to the retractor elements 151, 152, 153, 154, whether at least substantially attached and/or at least slidably-engaged to the retractor elements 151, 152, 153, 154, and a distal nexus or hub (or coupler) 199 for a distal point of an operable connection with the retractor elements 151, 152, 153, 154.

In some embodiments, the outer tube can have any dimensions believed to be useful to one of skill for the purposes taught herein. Examples of such dimensions are provided in U.S. patent application Ser. No. 13/913,466, incorporated herein in its entirety by reference as noted above.

The outer tube can be manufactured from any materials know to be useful to one of skill for the purposes taught herein. For example, the outer tube can comprise a polymer, or perhaps a polymer having embedded wire reinforcement. The wire reinforcement can be a mesh, a braid, a helical coil or any combination thereof. The wire reinforcement can include any material believed by one of skill to be useful for the purposes set-forth herein. Such reinforcements are also described in U.S. patent application Ser. No. 13/913,466. One of skill will appreciate that the outer tube should be flexible, elastically bendable, but sufficiently stiff torsionally to transmit torque from the handle or proximal end of the system to the retractor or distal end of the system.

The working space is formed to create a sufficient working distance for the tools for treatment, e.g., polyp dissection, to enhance maneuvering and manipulating the individual tools, enabling tissue triangulation. Working space distance is also advantageously formed to enhance visibility of the target tissue. The double bend described herein further enhances the working space.

As noted above, in some embodiments, the systems can include a multi-lumen catheter having at least 2 working channels for manipulating tools and an endoscope, each of the two working channels having 6 degrees of freedom that are independent from each other and the endoscope. The ability to independently manipulate the endoscope and tools allows, for example, one instrument to retract the tissue or lesion away or substantially perpendicular to another instrument, for example, the dissecting instrument, while independently optimizing the endoscope's position and, hence, the view of the treatment area. This would facilitate the removal of tissue with clear margins. The channels can manipulate the tools with several degrees of freedom, 6 degrees of freedom in some embodiments, providing a greatly enhanced maneuverability in the working area when compared to current state-of-the-art systems. In some embodiments, the at least one independently manipulable-and-articulable tool can be independently movable to various angles up to about 360 degrees.

FIGS. 1-8 illustrate how a system as taught herein can be positioned for treating a lesion in the ascending colon C, according to some embodiments. The description herein regarding removal of a polyp from the wall of the colon is shown and described by way of example as the system (as well as the other systems disclosed herein) can be used for other surgical applications and in other body spaces. The system can be inserted into the colon C in the non-expanded position of FIG. 1 to treat lesion 190 (FIG. 5). A lesion can be identified by endoscope 115. A sheath or cover can be positioned over the retractor elements 151, 152, 153, 154 to facilitate insertion, with the distal end of the sheath abutting the distal coupler 199 or alternatively overlying the distal coupler. After insertion to the target site, the sheath is removed to expose the retractor elements for subsequent expansion to the position of FIG. 3. In some embodiments, the retractor elements can be biased to an expanded position and retained in a collapsed delivery position by the sheath. In such embodiments, removal of the sheath to expose the retractor elements would enable the retractor elements to automatically expand to their expanded position of FIG. 3.

Expansion of the retractor elements 151, 152, 153, 154 creates a substantially symmetric working space 160 adjacent the lesion 190. The retractor 150 in some embodiments can be expanded by moving distal coupler 199 and proximal coupler 198 relative to one another, wherein as the distance between the couplers 199, 198, shortens, the retractor elements are forced more laterally with respect to the longitudinal axis of the outer tube (catheter) 105. In alternate embodiments, the retractor elements can be operably connected to an actuator such that the actuator is moved to bow the retractor elements such as in the embodiment of FIG. 11 discussed in detail below. In still other alternative embodiments, the retractor elements can be composed of a shape memory such as Nitinol or other material such that when exposed from the outer tube or from a sheath covering the outer tube, they automatically return to their expanded configuration, e.g., their shape memorized expanded configuration. When such shape memorized retractor elements are utilized, once exposed they would automatically move from the position of FIG. 1 to the position of FIG. 3.

The system 100 has (i) at least one independently manipulable scope 115, which can be articulable, to be used in viewing the lesion 190, (ii) at least one tool channel 110 for at least one independently manipulable-and-articulable tool 120, 125 to be used in the treating of the lesion 190, and (iii) the retractor 150. The retractor 150 can be located distal to the distal end 108 of the outer tube 105. The treating of the lesion 190 can include, for example, (i) viewing the lesion 190 with the articulating scope 115 and (ii) using the at least one tool 120, 125 in the treatment of the lesion 190 with a multidirectional and multi-angular approach to the lesion 190.

In some embodiments, the independently manipulable-and-articulable scope 115 and the at least one tool 120, 125 can be independently movable axially in the working area 160, independently rotatable in the working area 160, and independently bendable in at least one direction in the working area 160. The retractor provides a larger working area 160 for the treating of the lesion 190 without over-stretching, damaging or rupturing the colon.

Note that after the retractor system 150 is expanded as shown in FIG. 5, the endoscope 115 can be articulated in the working space 160 toward the target lesion 190 to improve visibility.

Figure 7:
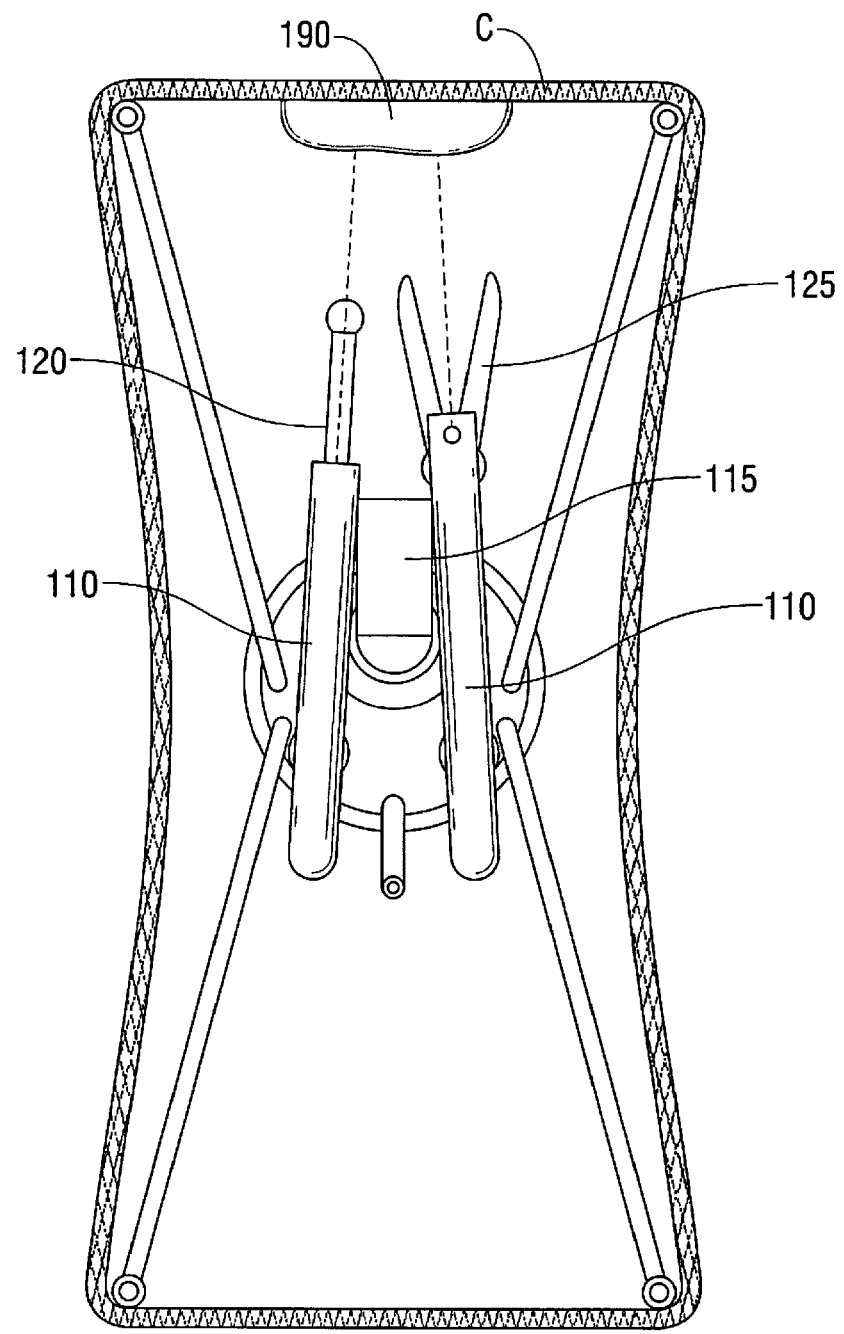
FIG. 7 is a front view of the system of FIG. 5.
Figure 8:
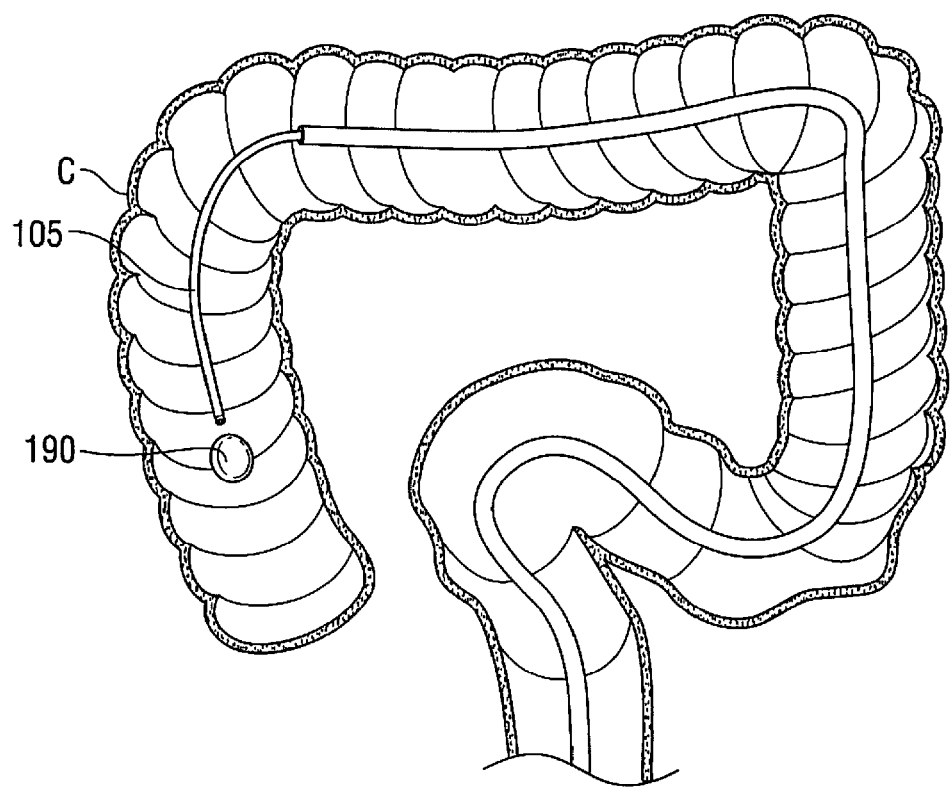
FIG. 8 illustrates the system inserted within the colon.
Figure 9:
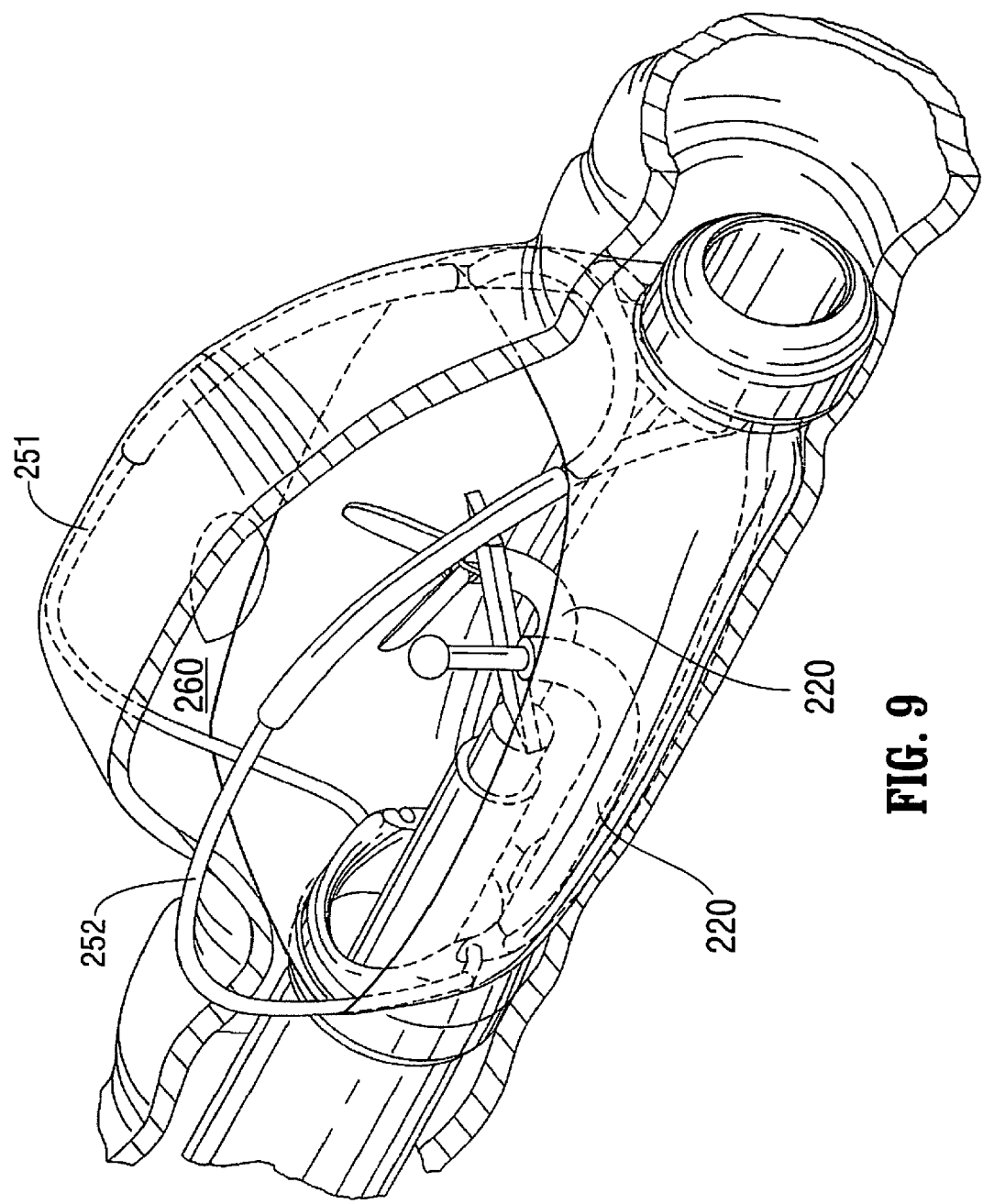
FIG. 9 illustrates a system of a copending commonly assigned prior application, the system shown to remove a lesion in a colon and having an asymmetric chamber, the colon shown in a cutaway view to show the system in perspective, wherein the retractor system is in the expanded position, the tool channels extend from the catheter and the endoscopic tools extend from the tool channels.
Figure 10A:
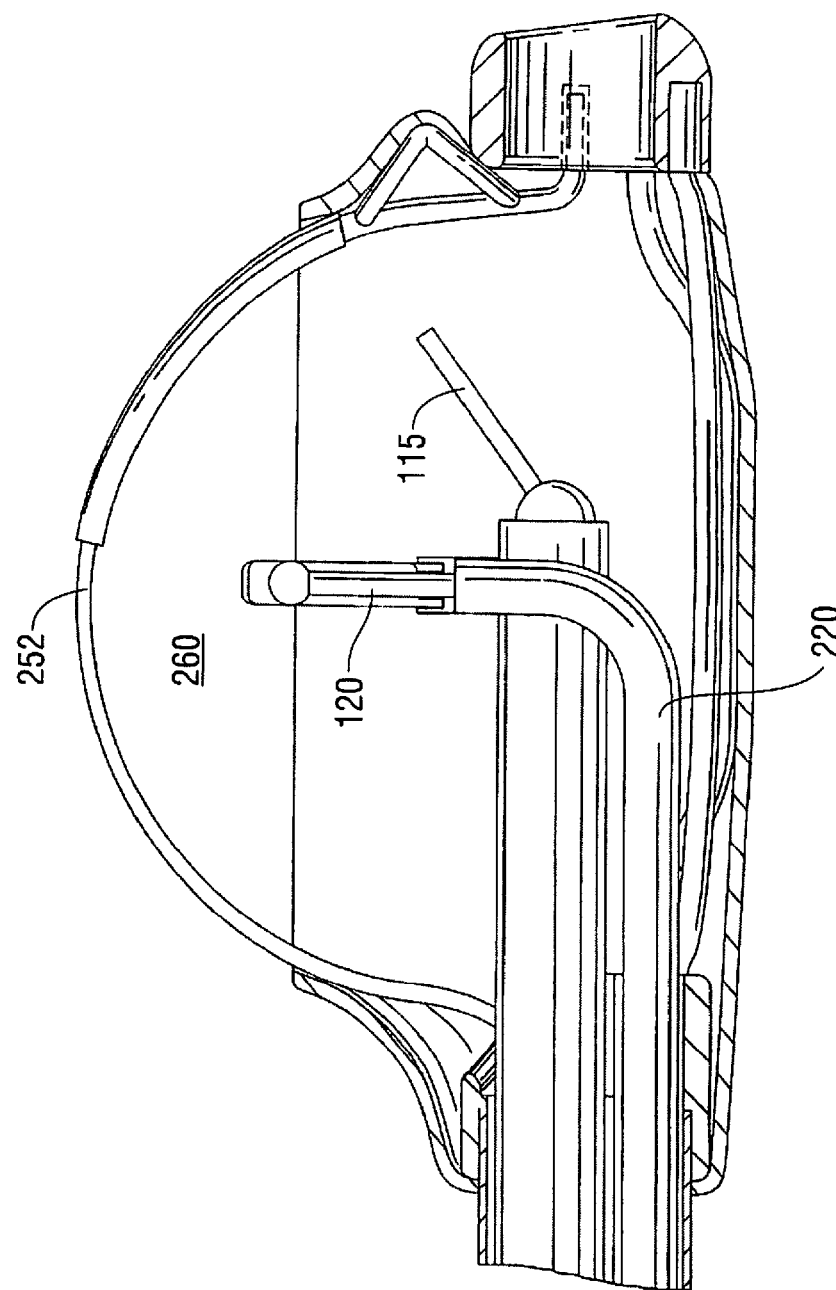
FIGS. 10A and 10B are side and front views, respectively, in partial cross section of the system of FIG. 9.
Figure 10B:
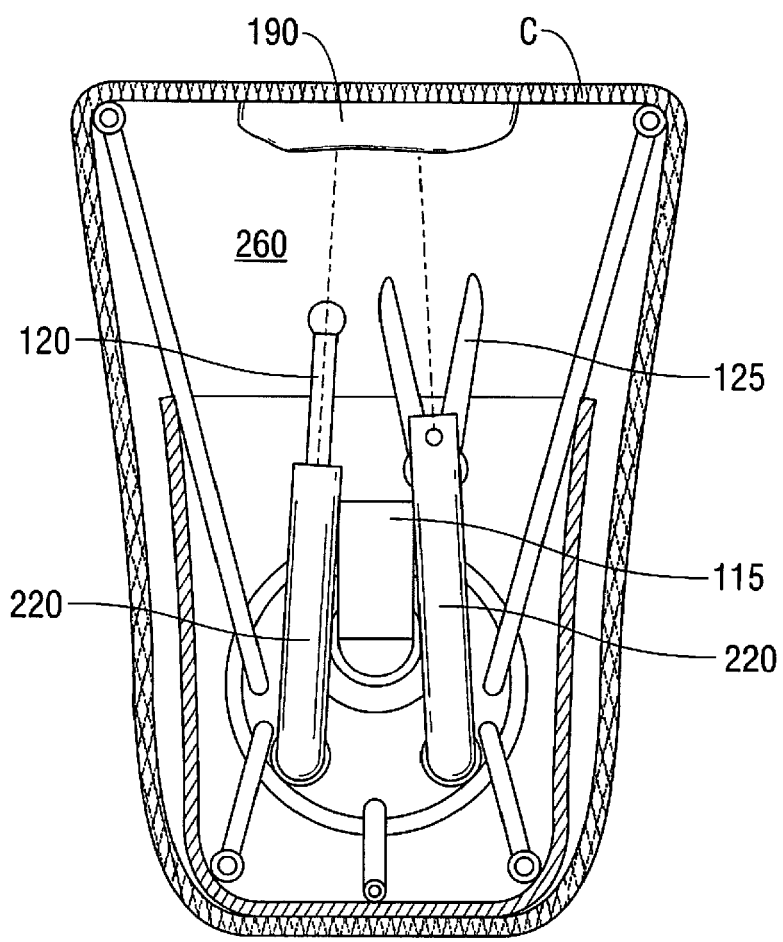

FIG. 5 illustrates a multidirectional and multi-angular approach to the lesion 190, showing the step of positioning the work area 160, endoscope 115, and tools 120, 125 in relation to the lesion 190. After the retractor 150 is expanded as shown in FIG. 5, the user of the system 100 can view and approach the lesion 190 with the tools 120, 125 from nearly any desired angle within the working space 160. The tool channels 110 as described above have a first bend or curve 112 extending away from lesion 190 to increase the distance from the lesion and a second bend or curve 114 extending toward the lesion 190 so endoscopic tools inserted through the tool channels 110 can be directed toward the lesion 190. In this manner, the distance from the tool channel opening to the lesion can be maximized and in some embodiments (by reducing the length of the tool channel distal of the second curve such as in FIG. 18A discussed below) be substantially equivalent to the distance from the tool channel opening to the lesion in the asymmetric chamber of FIGS. 9, 10A and 10B which illustrate the asymmetric chamber of copending commonly assigned application Ser. No. 13/913,466. By comparing the symmetric chamber with double curve tool channel 110 of FIGS. 5, 6 and 7 to the single curve tool channels 220 of the asymmetric working space 260 of FIGS. 9, 10A, 10B formed by retractor elements 251, 252 it can be appreciated that the respective distance to the lesion 190 is increased and in some embodiments can be substantially the same such that access, vision and maneuverability of the endoscopic tools is not compromised with the use of a symmetric chamber (the symmetric chamber expands less). Triangulation is also achieved as shown in FIGS. 7 and 10B.

Referring back to FIGS. 5-7, the tool channels 110 as shown are advanced through the respective lumens in the multi-lumen catheter or tube 105 and the endoscopic tools or instruments are inserted through the tool channels 110, with the distal ends of the tools extending distally of the respective tool channel 110. The advantages of the tool channels are described below in more detail in conjunction with the embodiment of FIG. 11, and such advantages are applicable to this and other embodiments utilizing the tool channels. As noted above, it is also contemplated that in alternative embodiments, the endoscopic tools can be inserted directly into the lumens of the catheter or tube, without the use of tool channels, provided they have the double bending/articulating characteristics described above which enable their manipulation without the use of bendable/articulatable tool channels.

As shown, the different angling of the tools 120, 125 advantageously achieves tissue triangulation to facilitate access, maneuverability and removal of the lesion. Note the dissection tool for excising the lesion 190 from the gastrointestinal tract can in some embodiments be in the form of an electrosurgical instrument, although other dissecting/excising tools can also be utilized. The excised lesion 190 can be released into the retractor assembly in preparation for completion of the procedure. The tool for excision of the lesion 190 can been replaced by another tool for closure of the lesion. The defect can be closed by various methods such as mechanical (e.g., clips staples or structures), glue, electrosurgical energy, etc. After capture of the lesion 190 in the retractor 150, the retractor can be collapsed to contain the lesion 190 within the collapsed retractor elements 151, 152, 153, 154 in preparation for removal of the system from the subject, including the use of an optional retractor cover which can be slid over the catheter to further encapsulate the lesion retained within the collapsed retractor elements.

The distal nexus or hub 199 is shown in the shape of a ring, although it can be virtually any shape desirable to one of skill, such as a cone, hemisphere, sphere, and the like, and it may or may not include a port for passage of the endoscope beyond the distal end of the system. As noted above, in some embodiments, the proximal coupler 198 can be moved toward the distal coupler 199, the distal coupler moved toward the proximal coupler 198, or both couplers moved toward each other to reduce their distance to force the retractor elements radially outwardly. The extent of outward expansion of the retractor elements can be controlled by controlling the distance between the proximal and distal couplers 198, 199, The retractor 150 can be repeatedly moved between expanded and retracted positions as desired by adjusting the distance between the coupler 198, 199. Such controlled expansion of the retractor elements can also be achieved by operatively coupling the proximal end of the retractor elements to an actuator as in the embodiment of FIG. 11. Alternatively, as noted above, the retractor elements can be composed of a material, e.g., shape memory material, to automatically expand when exposed from a catheter or sheath.

In some embodiments, the retractor can be reversibly stabilized by stiffening an otherwise flexible arrangement of the retractor 150 such as in the embodiment of FIG. 3. The stabilization of the retractor 150 can, in some embodiments, include a stabilizer having, for example, an at least substantially-rigid beam 175 to support the expanded retractor 150. The substantially rigid beam 175 can be substantially rectangular in cross-section, substantially circular in cross-section or of other cross-sectional shapes. It can be provided of the same or of a stiffer material than the retractor elements. It helps to create a more stabilized chamber as described herein. The beam 175 can be formed by the more rigid element exposed when the retractor elements are exposed from the outer tube for expansion, or alternatively, can be advanced independently from the outer tube or formed by advancement of a rigidifying structure. More than one of the retractor elements can have a rigidifying structure such that one or more of the retractor elements 151, 152, 153 and 154 can be stabilized.

In the embodiments of forming the rigidifying structure from a flexible beam, the rigid beam can be formed from a flexible beam, in some embodiments, by slidably inserting a rigid rod over a flexible tube that composes the flexible beam. More specifically, in this embodiment, the flexible beam slidably receives thereover a stabilizing or rigidifying structure such as a rigid rod. The rigidifying (stabilizing) structure can be independently actuated by the user by actuating a control, such as a slidable lever, operably connected to the rigidifying structure, such that movement of the actuator distally advances the rigidifying structure over the flexible beam to thereby stiffen the beam. Alternatively, the flexible beam can have a lumen to slidably receive therein a rigidifying structure such as a rigid rod. The structure in either version can optionally be retracted from the flexible beam to return the system back to the original more flexible state to aid collapsing of the retractor system. The beam can be substantially circular in cross-section, although other cross-sectional shapes are also contemplated. The rigid beam limits deflection of the distal end of the catheter which could otherwise occur by pressure exerted on the distal end by the body lumen wall. The at least substantially rigid beam prevents or inhibits deformation of the retractor during creation of forces on the retractor in the expansion and prevents or inhibits bending of the catheter tip. The forces include forces from expanding tissue outwards as well as the initial forces applied on the retractor elements to create the working space. The rigid rod can be a straight component comprising a rigid material, for example stainless steel or another metal or alloy, that is slidable in and out of the inner diameter (lumen) of the flexible tube (or alternatively over the outer diameter of the flexible tube). The rigid rod can be pushed forward (i.e., orally) into (or alternatively over) the flexible tube to stiffen and straighten the flexible tube as in the embodiments described above. By pushing the rigid rod across the length of the flexible tube, the flexible tube, or flexible beam, becomes rigid and straight, and in effect renders the whole retractor structure at least substantially rigid and straight to stabilize the retractor system. The flexible tube, or flexible beam, may also comprise a series of rigid tubes having a flexible, non-stretchable cable passing through the lumens of the tubes. When the cable is relaxed, the series of rigid tubes can be separated using, for example, a compressible component such as a spring between each of the series of rigid tubes to provide a flexible non-overlapping configuration. When the cable is tensioned, the compressible components compress, and the rigid tubes overlap, converting the flexible beam into a rigid beam. Such alternative mechanisms can be utilized with any of the embodiments described herein. Thus, during insertion of the system into a tortuous body lumen, for example a colon, the retractor can be unexpanded and flexible. This flexibility allows the retractor to bend to conform to the bends in the tortuous body lumen, so that it can be advanced with ease and not cause trauma to the lumen. Once the retractor is advanced to the target location in the lumen, the flexible beam of the retractor can be straightened and stiffened as described herein. Since the system can be flexible and torsionally stiff, the proximal shaft or the handle can be easily rotated as desired relative to the location of the target lesion.

In some embodiments, the flexible beam can include a polymer. The flexible beam can be, for example, a flexible tube that is reinforced with metal wires, braids, or coils that include, for example, a metal such as a stainless steel or NITINOL. In some embodiments, the flexible tube can be kink resistant and transmit torque. And, in some embodiments, the flexible tube can comprise a combination of both flexible sections and rigid sections. In these embodiments, a flexible section can lie-between rigid sections, for example. Such flexible tubes can include composites of overlapping tubes joined using any method known to one of skill, including bonding using epoxy or cyanoacrylates, in some embodiments.

Figure 3A:
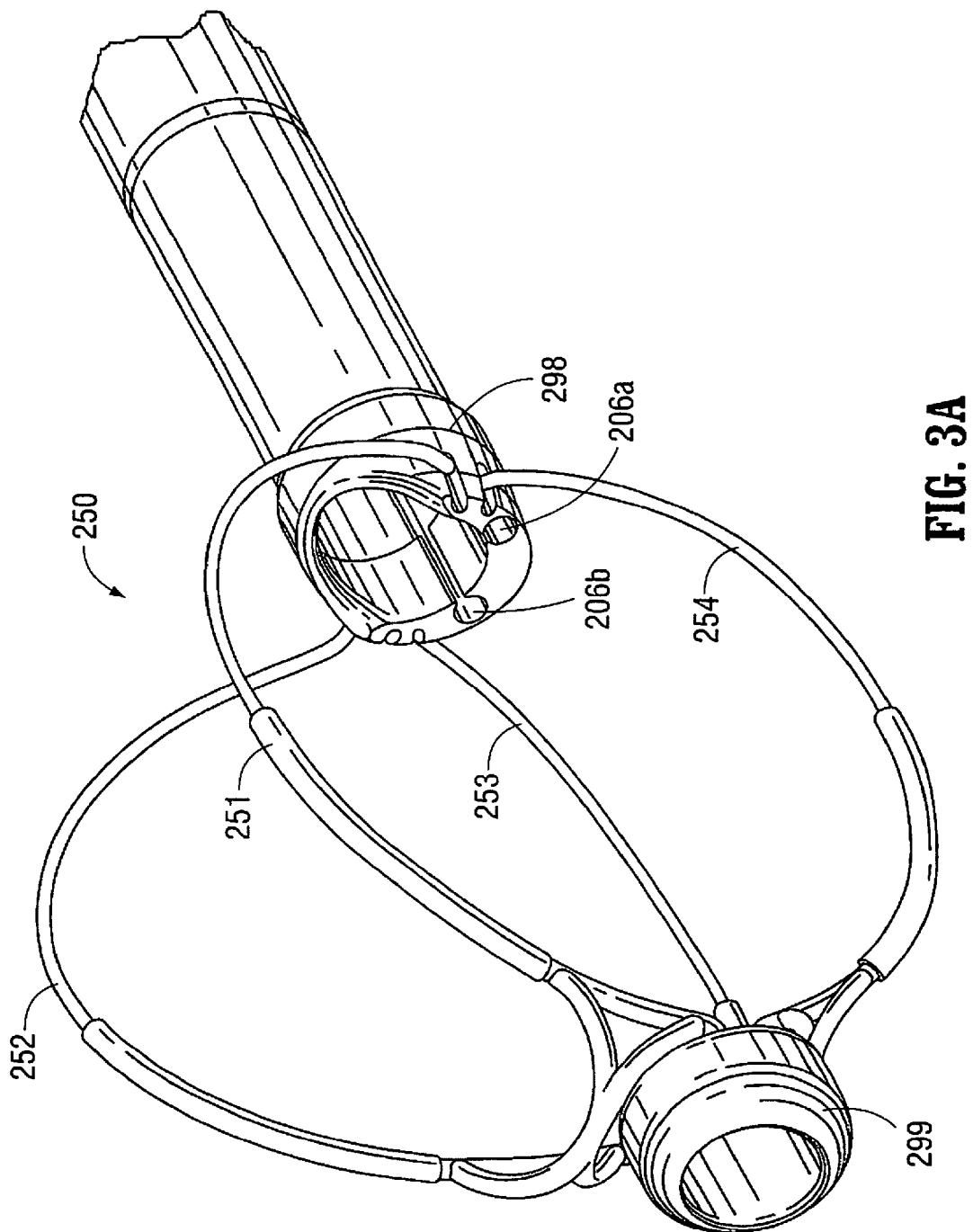
FIG. 3A is an alternate embodiment of the retractor system shown in the expanded position.
Figure 4:
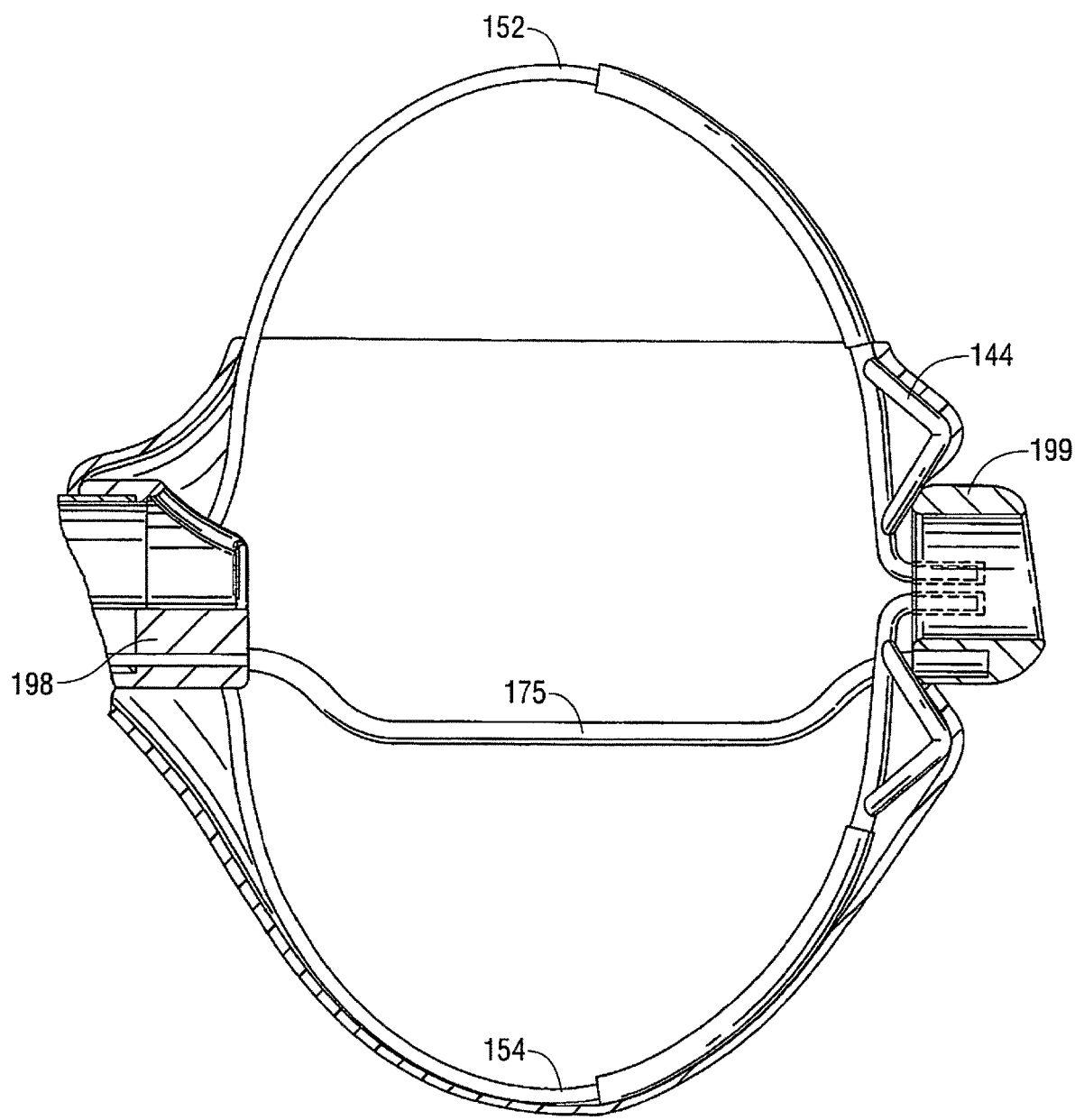
FIG. 4 is a side view of the retractor system of FIG. 3.

FIG. 3A illustrates an alternative embodiment of the retractor system 250 which is identical to the retractor system 150 of FIG. 3 except a rigid beam is not provided. Otherwise the components are identical to the retractor system 150 and are labeled for convenience in the "200" series so the system 250 includes retractor elements 251, 252, 253 and 254, proximal hub 298, distal hub 299 and tool channel (or instrument) lumens 206a, 206b.

A bridge member can be utilized to add stability to the retractor. For example, the retractor system 150 can include a bridge member 144 configured to maintain a desired orientation of the retractor elements during the expansion, the bridge member 144 operably stabilizing at least two 151, 152 of the four retractor elements 151, 152, 153, 154. That is, in the embodiment of FIG. 3, the bridge member 144 is attached to the two retractor elements 151, 152. The bridge member 144 creates a transverse structure for the elements 151, 152, limiting side-to side movement. Bridge member 144 can also include a second bridge section connected to bridge 144 and to retractor elements 153 and 154 thereby connecting all four retractor elements 151, 152, 153, 154. The bridge member 144 can be a separate component or alternately integrally formed with one or both of the retractor elements 151, 152. The bridge member can be composed of a material similar to the elements 151, 152 or can be composed of a different material.

Additional bridge members can be provided on the retractor elements to increase stability. Note that one or more bridge members can be used with the other retractor embodiments disclosed herein.

In some embodiments, the bridge member 144 can be configured to reduce drag from surrounding tissue during use. For example, the bridge member 144 can be configured to facilitate a movement of the system in a gastrointestinal tract by designing the bridge member 144 to include a forward component 144a that is inclined to facilitate forward movement orally, and a reverse component 144b that is inclined to facilitate reverse movement anally.

In some embodiments, the bridge can be designed to flex to prevent the retractor elements from collapsing towards each other or bending away from each other, while also providing some spring or elasticity to the system to comply gently with the tissue. One of skill will appreciate that the bridge can comprise any suitable material that provides the material characteristics desired. For example, the bridge can be formed from a curved nitinol wire. The ends of the nitinol wires can be connected to the retractor elements using any manufacturing process deemed including, for example, tubing connectors, adhesives, or solder.

The systems taught herein can have an outer tube that is wire-reinforced, such as mesh, braided, or the like, to provide kink resistance and torqueability to the system, as well as to further facilitate a positioning of the system in the subject.

FIG. 3 shows multiple lumens 106a, 106b. Central lumen 106c can contain an endoscope such as endoscope 115 described above. Lumen 106b can contain a first working channel for a first endoscopic tool, and lumen 106a can contain a second working channel for a second endoscopic tool. The working channels can receive the first and second tools directly therein, or alternatively, receive tool channels (tool guides) described herein for angling the endoscopic tools slidably positioned therein.

The term "tool channel" can be used interchangeably with the term "working channel" or tool guide." In some embodiments, a channel can be a separate component placed inside the outer tube, or it can be a space remaining in the lumen of the outer tube between separate components that were placed in the outer tube, the separate components including, for example, an endoscope, a working channel, an instrument, a guide, and the like.

The retractor elements can have a covering, which add bulk to the retractor elements 151, 152, 153, 154 by increasing its cross-sectional diameter. The covering 151a, 152a, 153a, 154a (FIG. 3) extends over an intermediate portion of the respective retractor elements and can be in the form of a heat shrink tubing. The covering helps control expansion by providing a less flexible region.

During insertion of the system into a tortuous body lumen, for example a colon, the retractor can be unexpanded and flexible. This flexibility allows the retractor to bend to conform to the bends in the tortuous body lumen, so that it can be advanced with ease and not cause trauma to the lumen. Once the retractor is advanced to the target location in the lumen, the flexible beam of the retractor, if provided, can be straightened and stiffened as described herein. Since the system can be flexible and torsionally stiff, the proximal shaft or the handle can be easily rotated as desired relative to the location of the target lesion.

The endoscope and tools can be maneuvered independently, for example, to access the lesion at a greater range of angles and improve the view of the lesion and ability to manipulate and dissect the lesion. For example, a grasper can be advanced out of the instrument channel into the working space and flexed towards the polyp, grasp the polyp and retract the tissue to expose the base of the polyp for dissection by a dissection tool through the multi-channel systems taught herein.

In an alternate embodiment, the system can be floating in the outer tube to enhance flexibility for positioning the system in a subject. Such floating system is described in commonly assigned co-pending U.S. application Ser. No. 13/531,477, filed Jun. 22, 2012. During use of such floating system, the working (floating) channel and/or endoscope are floating such that they are (i) at least substantially attached to the lumen of the outer tube at a first proximal location (not shown) and a first distal location and (ii) at least substantially floating in the lumen of the outer tube between the first proximal location (not shown) and the first distal location. The separate floating components increase the flexibility and facilitate positioning the system in the subject for the treatment of the target tissue.

Each tool channel can be operatively connected to a handle in a manner as described below with respect to the embodiment of FIG. 11. Also, in some embodiments, an actuator is provided to control the angle of the tip by controlling the degree of proximal retraction of the pull wire, with further retraction further bending the tip and less retraction bending the tip to a lesser degree. More than one tool channel can be provided, and the multiple tool channels can be controlled by a single actuator, or alternatively, a separate actuator can be provided for each tool channel. Also, various mechanisms can be utilized to lock the actuator(s) in position to maintain the bent position of the tip of the tool channels.

Other mechanisms can also be utilized to control the tool channels. Alternatively, one or more of the tool channels can have the pre double bent (double curve) tip which is substantially straight when in the insertion position within the confines of the multi-lumen tube (catheter) and returns to the double bent position when exposed from the confines of the catheter.

As described herein, the channels or guides (flexible tubes) can be configured to control the trajectory and position of instruments such as forceps in the working space created by the retractor. In some embodiments, a channel can be removed from, or inserted through, the outer tube of the system. The channels can be virtually any size considered by one of skill to be useful in the systems described herein. For example, a channel can have an inner diameter ranging from about 1 mm to about 5 mm, from about 2 mm to about 4 mm, from about 1 mm to about 3 mm, or any range therein. The length of the channel should, of course, complement the length of the system. For example, the channel can have a length ranging from about 40" to about 72", from about 48" to about 60", from about 42" to about 70", from about 44" to about 68", or any range therein in increments of 1".

The channels can also comprise any material or configuration known to one of skill to be suitable for the uses described herein. For example, the channels can comprise a single polymer layer, multiple polymer layers, a wire reinforced layer, or a combination thereof.

For flexing the distal end of the channel, there can be a side lumen with a pull wire embedded between the inner layer and the outer layer. In some embodiments, the side lumen can be located between the inner layer and the reinforcement layer, or the side lumen can be a part of the inner layer. The tool (working) channels (flexible tubes or guides) positioned inside the outer tube provide a multi-lumen catheter having manipulable passages for independently manipulating tools from outside the body into the working space inside created by expansion of the retractor.

In some embodiments, two inner tubes can be positioned adjacent to the inner surface of the outer tube to provide, effectively, three separate channels. The two inner tubes can function as two independent tool channels while the space between these first two channels and the outer tube functions as a third channel. The third channel can be substantially larger than the other two channels. In some embodiments, the largest diameter channel can be the channel for the endoscope.

The inner tubes can be composed of various materials, such as a fluoropolymer such as TEFLON for lubricity to ease tool or endoscope passage and movements. Other materials that may be used include, for example, polyethylene, polypropylene, PEBAX, nylon, polyurethane, silicone, and composites thereof, each of which may also be used with a lubricant coating. The tubes may also comprise a metallic wire reinforcement such as a braid, mesh or helical coil, each of which may be embedded in the tube.

The systems provided herein can be used in several different methods of treatment. For example, the systems can be used in a method of treating a gastrointestinal lesion using a multidirectional and multi-angular approach to the lesion. The method can include positioning the system in a subject's gastrointestinal tract, the positioning including placing the retractor in proximity to a target lesion for a treatment; expanding the retractor to create the treatment space for use of the tool; treating the lesion with the tool; collapsing the retractor; and, withdrawing the system from the subject. The lesion can include, for example, a perforation, a tissue pathology a polyp, a tumor, a cancerous tissue, a bleed, a diverticuli, an ulcer, an abnormal vessel, or an appendix.

In some embodiments, it is desirable to provide a cover or sheath that covers a portion of the system, including the retractor during delivery of the retractor to a target site, during a treatment of a target tissue at the target site, during a removal of the target tissue, and/or during a removal of the system from the subject, or a combination thereof. One of skill will appreciate that the retractor has elements (including the bridge members) that can catch, snag, or otherwise disturb or contact tissue during delivery, or removal, of the retractor to or from the target site. The sheath covers a collapsed configuration of the retractor 150 to render an at least substantially smooth and/or atraumatic surface for a delivery of the retractor 150 to a target site (not shown) for a treatment of a target tissue (not shown). Also, the treatment of the target tissue may include, for example, a dissection of tissue that can be performed within the cover without intermingling the target tissue with the surrounding tissues. Moreover, the dissected tissue may be a cancerous or other tissue that is desirable to contain during treatment or removal by encapsulating it within the cover. Thus, the sheath forms a collection means for entrapping and/or pulling out resected tissue. The terms "cover" and "sheath" can be used interchangeably, and one of skill can appreciate that such embodiments are open to improvements, as taught herein.

In some embodiments, the sheath is clear and is attached at one end to the distal hub or coupler and extends proximally past the proximal coupler or hub and is attached to the outer surface of the catheter. Alternatively, the sheath can be attached at a proximal end to proximal coupler. The sheath can be at least substantially closed around the retractor 150 during delivery, and can be designed to open as the retractor 150 is expanded to create the working space 160 for the treatment. Alternatively, the expansion of the retractor elements and the sheath can be independent.

In some embodiments, the sheath can be perforated longitudinally (not shown), designed such that the sheath opens upon expansion of the retractor through tearing of the perforation at the target site. In some embodiments, a tongue-and-groove mechanism, for example a ZIPLOCK mechanism, can be used to at least substantially close a slit at the top of the retractor which can also open upon the expansion of the retractor at the target site. In some embodiments, a larger perforation, or unclosed portion, can remain in the sheath to facilitate the tearing or opening of the sheath at the target site upon the expansion of the retractor 150. In some embodiments, the terms "slit" and "opening" can be used interchangeably.

In some embodiments, the sheath can be reversibly opened, such that the sheath can be re-closable. For example, a drawstring, cable, or wire, can be operably positioned in communication with the opening for the re-closing of the opening by pulling or pushing the drawstring, cable, or wire from outside the patient during the treatment. In some embodiments, the edges of the opening can form longitudinal pockets or channels for pulling or pushing the drawstring, cable, or wire as desired from outside the patient during the treatment, such as by routing the drawstring, cable, or wire through the system and, perhaps, through the handle as with the other actuation means. In some embodiments, a drawstring is used to re-close the sheath, wherein the strings can be tensioned at the handle to close the slit, or loosened to allow the retractor to expand. In some embodiments, the sheath has a stiffening strip running transversely around the mid portion of the cage to facilitate the cage wires expanding without catching on the surrounding sheath. The stiffening strip can be another layer of the sheath welded or glued onto the existing sheath. It can also be formed as a thickened area. Alternatively, a stiffer material can be inserted in the pocket running transversely. The stiffening material may be the same as that of the sheath.

In use, in some embodiments, when the retractor system is moved from the collapsed insertion position to the expanded position, the expandable retractor elements are expanded away from the sheath. The sheath can remain open at a surface facing the target tissue to be treated, e.g., removed, from the patient's body. Alternatively, the sheath can remain closed and be opened by an endoscopic tool to receive the removed lesion.

FIGS. 11-30 illustrate alternative embodiments of the system, designated generally by reference numeral 1100. System 1100 includes a multi-lumen catheter or tubular member 1110 configured to receive one or more tool channels or instrument guides (also referred to herein as flexible tubes). FIG. 11 shows two tool channels 1122 and 1124, it being understood that in some embodiments, only one tool channel can be utilized and in other embodiments more than two tool channels can be utilized, with the catheter provided with a sufficient number of lumens. The tool channels 1122, 1124 can be packaged as a kit with the catheter 1110 as shown in FIG. 11. Alternatively, the tool channels 1122, 1124 can be packaged separately. In other embodiments, the tool channels are packaged already inside the lumens of the catheter 1110. Each tool channel 1122, 1124 has a lumen (channel) to receive an endoscopic instrument (tool) therethrough.

Figure 16:
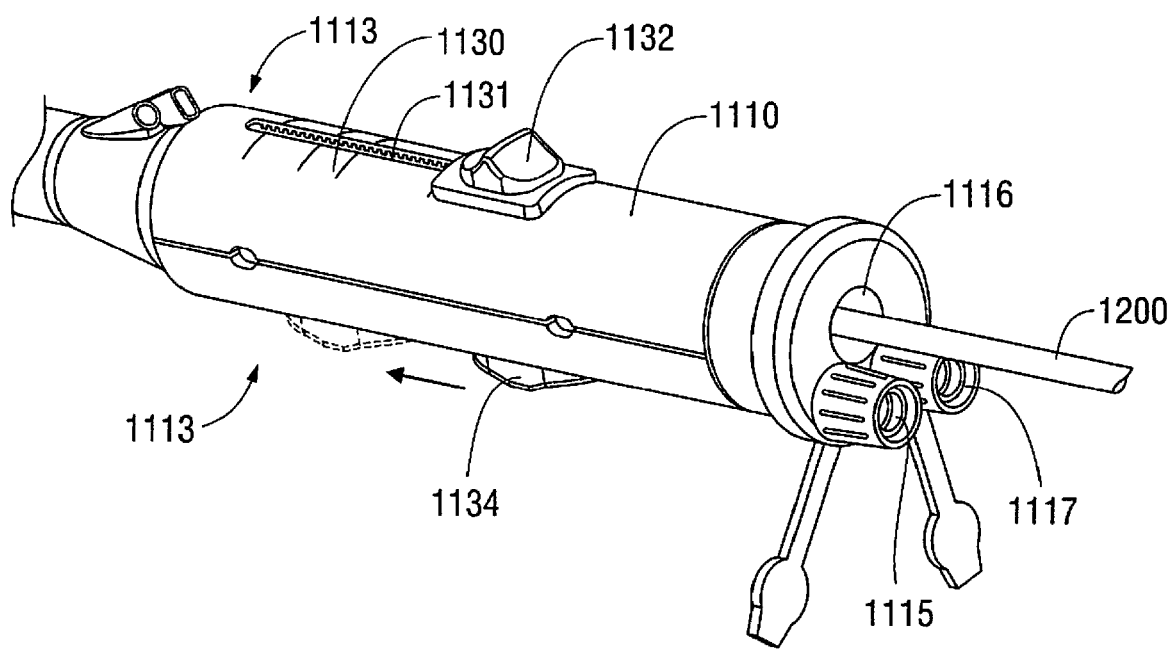
FIG. 16 is a perspective view of the proximal end of the catheter of FIG. 11.

Tool channel 1122 has a double curve (bend) at its distal tip 1122*a* defining a first curve (bend) 1122*b* extending away (downwardly as viewed in the orientation of FIGS. 11 and 18) from the longitudinal axis and then transitioning into a second curve 1122*c* extending in a second opposite direction (upwardly as viewed in the orientation of FIGS. 11 and 18) toward the longitudinal axis. Tool channel 1124 similarly has a double curve (bend) at its distal tip 1124*a* defining a first curve (bend) 1124*b* extending away (downwardly as viewed in the orientation of FIGS. 11 and 18) away from the longitudinal axis and then transmitting into a second curve 1124*c* extending in a second opposite direction (upwardly as viewed in the orientation of FIGS. 11 and 18) toward the longitudinal axis. The first curve increases the distance from the distal opening 1122*d*, 1124*d* of the tool channel to the target lesion as compared to a single curve which does not have a downward bend. The tool channels (flexible tubes or guides) 1122 and 1124 are inserted through the proximal end of the catheter 1110 and advanced through respective lumens 1112, 1114 in the catheter 1110 (see FIG. 12). As shown in FIG. 16, which illustrates a proximal portion 1113 of catheter 1110, the catheter 1110 can include ports 1115, 1117, cooperating with the lumens 1112, 1114, respectively (FIG. 12), which can include valves to maintain insufflation when the tool channels 1122, 1124 are inserted therethrough and translated axially therein.

When the tool channels 1122, 1124 are inserted into the lumens 1112, 1114 of catheter 1110, the pre-bent tips 1122a, 1124a are preferably substantially straightened to facilitate advancement through the lumens. When the tool channels 1122, 1124 are advanced sufficiently distally so the distal tips 1122a, 1124a are exposed from the confines of the walls of the catheter lumens 1112, 1114, the tips 1122a, 1124a, return to the pre-set double curved position. This can be understood with reference to FIG. 18 which illustrates in phantom the straightened position of the tool channels 1122, 1124 for movement within the catheter 1110. As in the other embodiments disclosed herein, the tool channels 1122, 1124 can be composed of superelastic material, although other materials to provide the curved tip which returns from a substantially straight insertion shape to a curved shape when exposed can also be used, such as stainless steel. Also, as in the other embodiments disclosed herein, shape memory properties of material such as Nitinol can be used with a memorized curved tip shape. In alternative embodiments as described above, the tool channels 1122, 1124 can have a mechanism such as a pull wire which is actuated to bend its distal end. The tool channels 1122, 1124 in the embodiments of FIGS. 11-30 are unattached to the catheter 1110 so that the user can freely control their axial movement from a proximal end portion 1122b, 1124b, during use. However, it is also contemplated that in alternate embodiments the tool channels can be attached to the catheter, e.g., attached at proximal and distal ends to provide floating channels.

The tool channels 1122, 1124 can optionally include markings 1123, 1125, respectively, at a region proximal to the catheter 1110 to provide a visual indicator to the user of the depth of insertion of the tool channels 1122, 1124 through the catheter lumens 1112, 1114. The tool channels 1122, 1124 can have a luer fitting 1127, 1129, respectively, (FIGS. 11 and 19A) with a valve, at the proximal end which can close off backflow of insufflation gas from the body. This maintains insufflation when the endoscopic tool is inserted through the tool channels 1122, 1124 as described below. The tool channels in an alternate embodiment shown in FIG. 19B have a hemostatic valve 1121A, 1121B connected at a proximal end of tool channels 1122', 1124', respectively, to maintain insufflation during tool insertion. As shown, valves 1121A, 1121B are proximal of luer fittings 1127', 1129'. The tool channels 1124', 1126' are identical to tool channels 1124, 1126 in all other respects.

Figure 18:
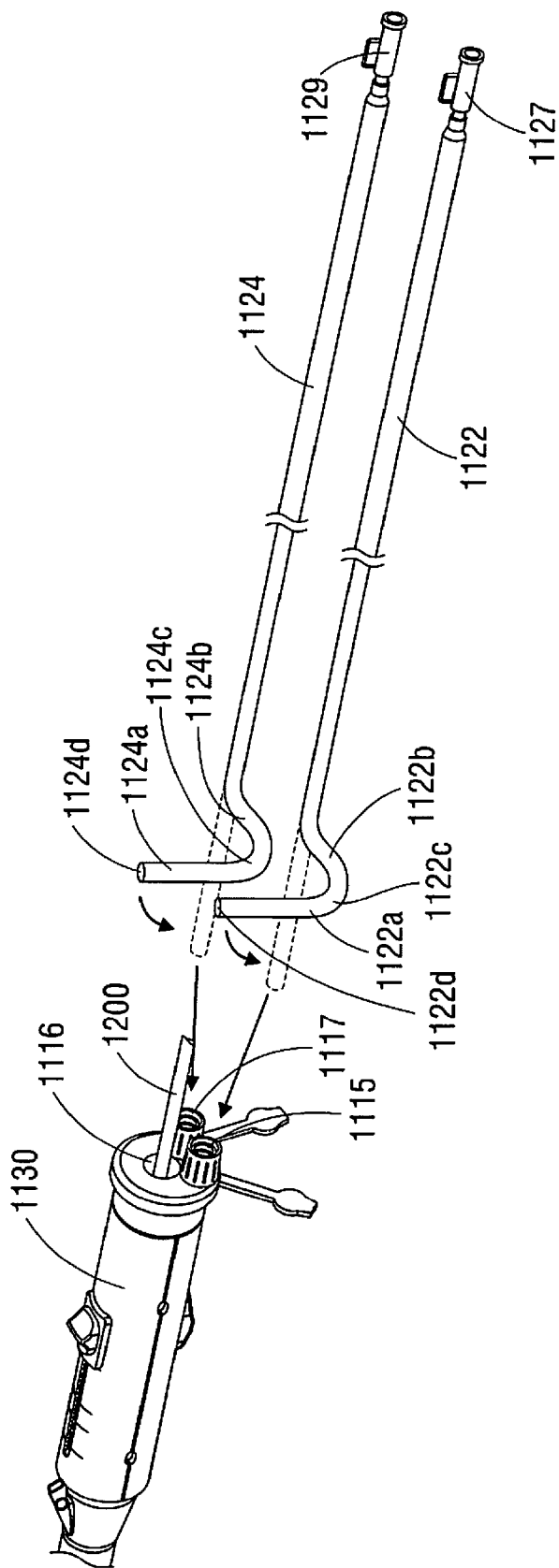
FIG. 18 is a perspective view showing the two tool channels (guides) adjacent the proximal end of the catheter of FIG. 11 for insertion therethrough.
Figure 18A:
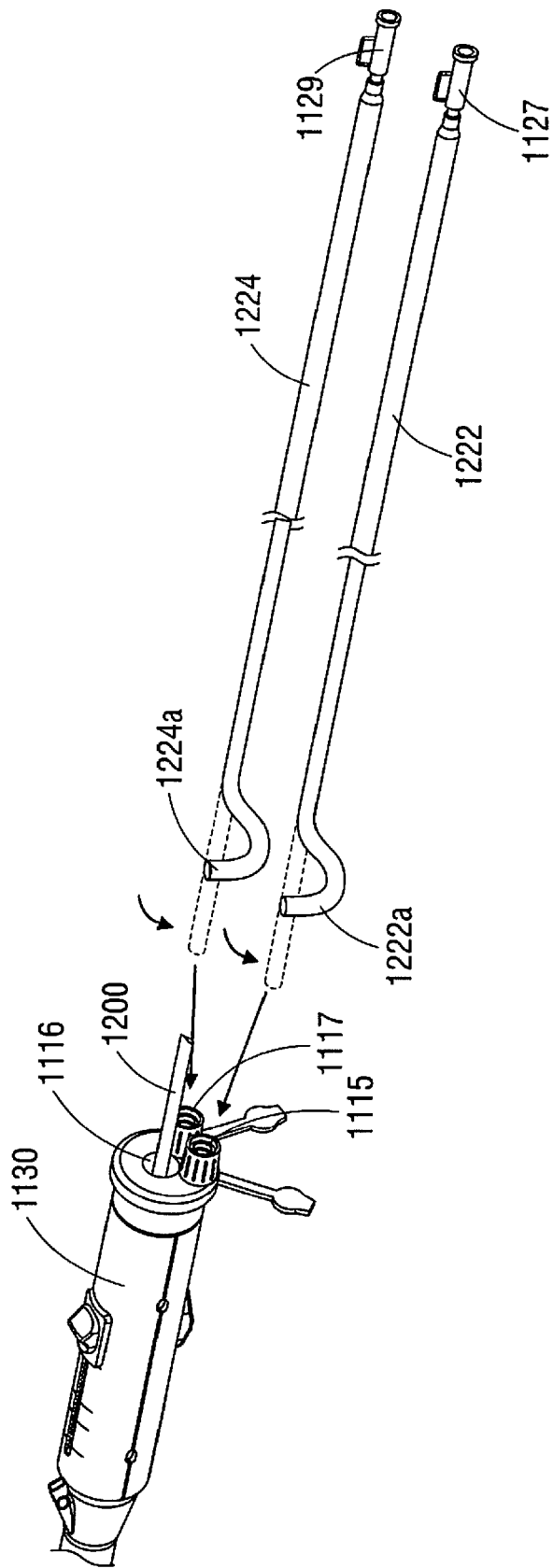
FIG. 18A is a perspective view similar to FIG. 18 showing an alternate embodiment of the tool channels.

In the embodiment of FIG. 18, the distal tip of the tool channels 1122, 1124 extend radially beyond the longitudinal axis of the tool channel 1124, 1126 so the distal opening is beyond the axis. In the alternate embodiment of FIG. 18A, the distal tip 1222a, 1224a does not extend radially beyond the longitudinal axis so the distal opening is substantially aligned with the longitudinal axis of the tool channels 1124, 1126. This reduced length after (distal) the second curve increases the distance from the distal open to the lesion and in some embodiments can be substantially equivalent to the distance obtained with the asymmetric chamber discussed above. The tool channels of FIG. 18A are otherwise identical to the tool channels of FIG. 18. Alternatively, the distal opening of the tool channels could be below (as viewed in the orientation of FIG. 18A) the longitudinal axis of the tool channels to further increase the distance from the distal opening to the target lesion.

In one embodiment, the tool channels 1122, 1124 can be composed of a flexible soft material, such as Pebax. A superelastic nitinol backbone can in some embodiments be embedded in the wall of the Pebax material, e.g., within the curved portion. Other materials are also contemplated.

Catheter 1110 also preferably has a lumen 1116 (see e.g., FIG. 16) configured and dimensioned to receive an endoscope 1200. In some embodiments, the lumen 1116 is dimensioned to receive a conventional endoscope, e.g., a conventional colonoscope, and the catheter 1110 is backloaded over the endoscope. This is described in more detail below in conjunction with the method of use. In alternate embodiments, the lumen 1116 can receive an articulating endoscope. Moreover, in alternate embodiments, the endoscope can be inserted into the catheter and inserted into the body lumen.

Figure 11:
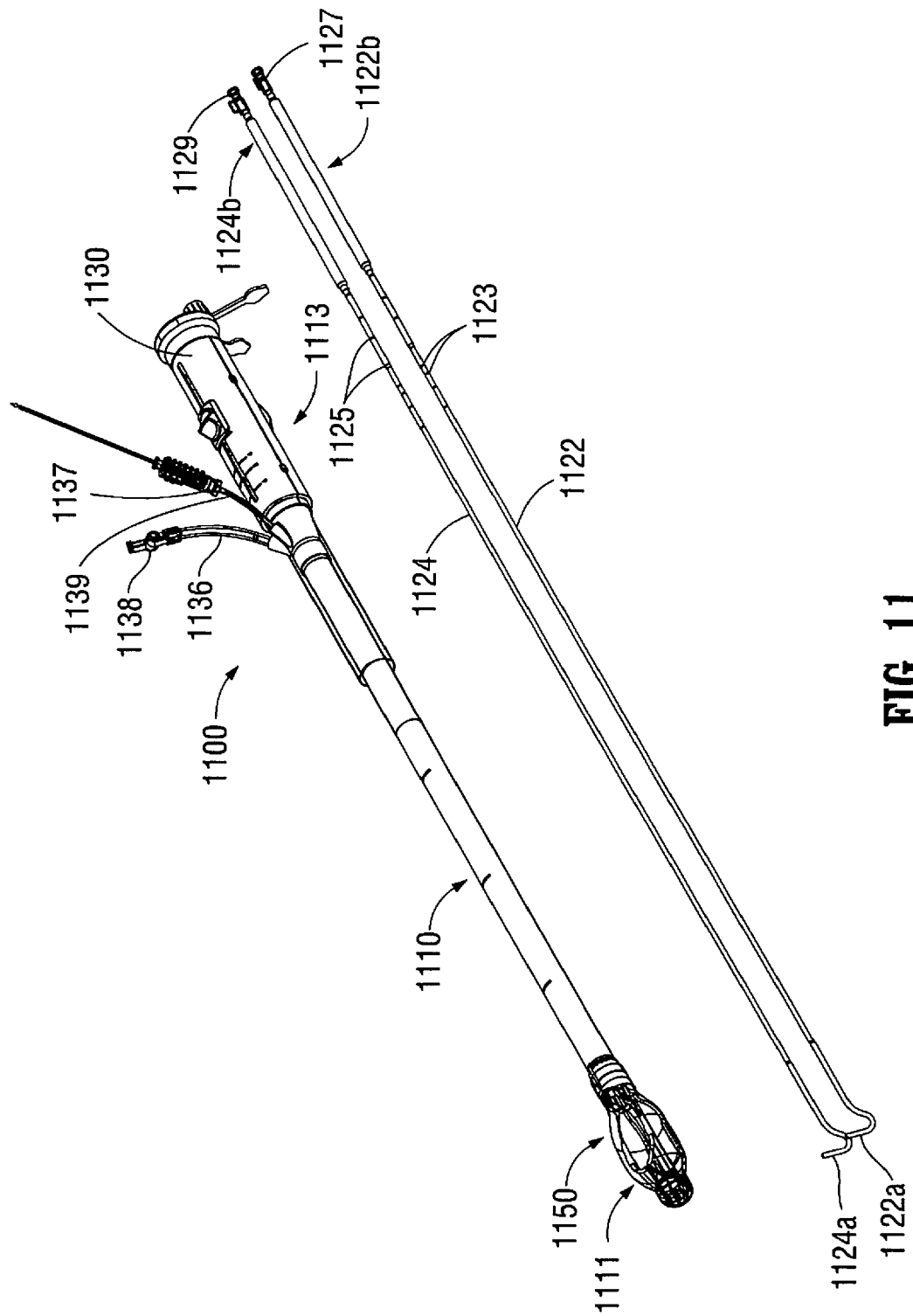
FIG. 11 is a perspective view of an alternate embodiment of the system showing the catheter and two tool channels.
Figure 31A:
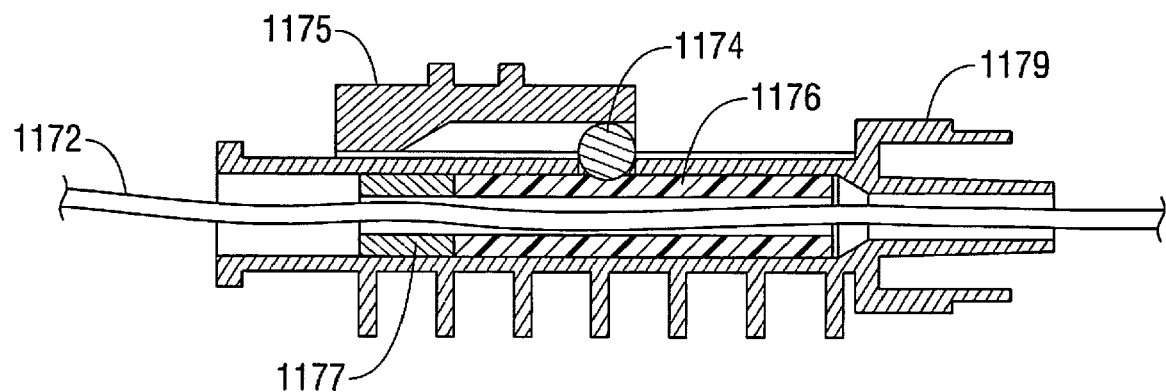
FIGS. 31A and 31B are cross-sectional views illustrating the switch for retaining the suture for closing the covering (bag).
Figure 31B:
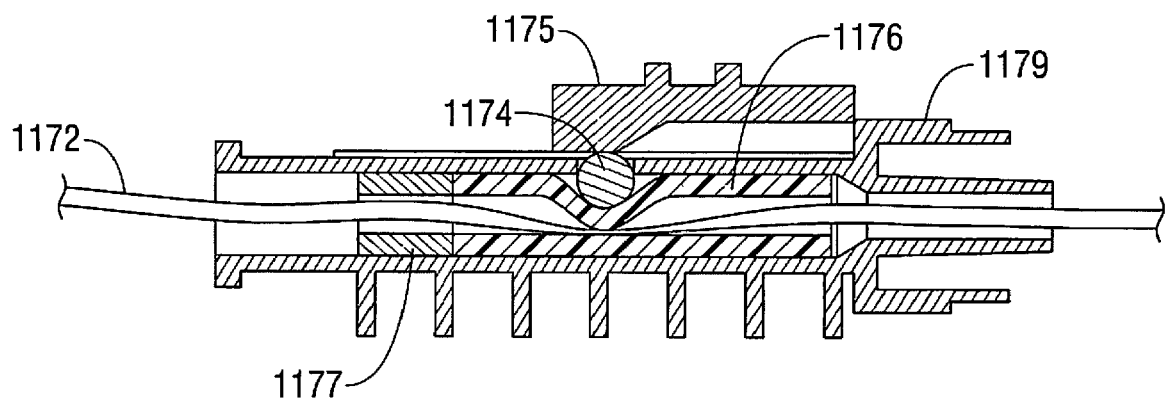

With reference to FIGS. 11 and 16, catheter 1110 includes a handle housing 1130 at the proximal portion 1113 which contains two actuators: actuator 1132 for controlling movement of the retractor system 1150 and actuator 1134 for controlling movement of the rigidifying (stabilizing) structure, if provided. Catheter 1110 also includes tubing 1139 having a luer coupling 1137 and a control switch 1175 (see FIGS. 31A, 31B) for closing off an internal gasket 1176. The suture 1172 for closing covering 1170 is secured by the elastomeric gasket 1176 as the switch 1174 is moved from the position of FIG. 31A to the position of FIG. 31B. More particularly, in the initial position of FIG. 31A, the ball valve 1174, seated in a slot in the housing 1179, does not apply a force to the gasket 1176. This enables the suture 1172 to freely move within the lumen of the catheter. When it is desired to lock the suture 1172 in position, i.e., after the suture 1172 is tensioned to close the covering 1170, the switch 1175 is slid forward, thereby camming the ball 1174 downwardly (as viewed in the orientation of FIG. 31B) to collapse the lumen in the gasket 1176 against the suture 1172 to thereby secure the suture 1172. This locks the suture 1172 against movement which thereby maintains the covering (bag) in the closed position encapsulating the target tissue as described herein. Note that the reverse movement of the switch 1175 unlocks the suture 1172 to enable free movement of the suture 1172. Catheter 1110 also has tubing 1136 having a one-way stopcock 1038 to provide an insufflation port. This port can be used to supplement the insufflation gas provided by the endoscope 1200. The insufflation gas flows through lumen 1116 in the area around the endoscope 1200 since the cross sectional dimension of the lumen 1116 exceeds the cross-sectional dimension of the endoscope 1200 to leave a sufficient gap. As shown, the tubings 1139, 1136 are positioned distal of the actuators 1132, 1134.

Figure 12:
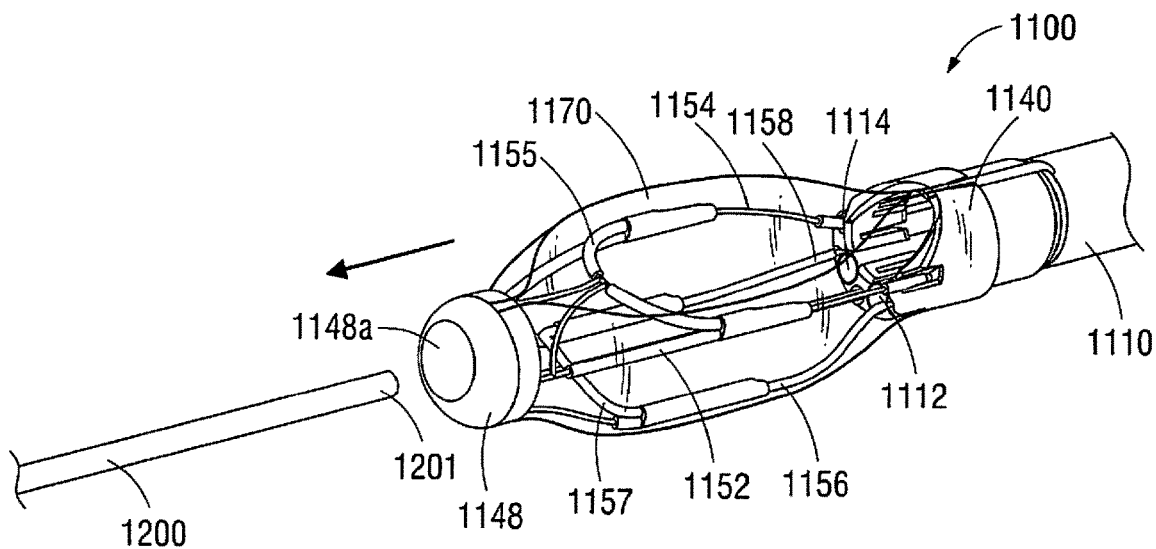
FIG. 12 is a perspective view of the catheter of FIG. 11 being inserted over the proximal end of the endo scope of FIG. 13 (prior to insertion of the endoscope into the colon), the retractor system shown in the collapsed position.

Turning now to the retractor system 1150, which forms a body lumen reshaping or reconfiguring system, and with initial reference to FIG. 12, the retractor system 1150 is positioned at the distal portion 1111 of the catheter 1110 (distal of proximal hub 1140) and includes flexible retractor elements 1152, 1154 1156 and 1158. Retractor elements 1152, 1154, 1156, 1158 form the expandable elements which create the working chamber (space) within the body lumen and form a substantially symmetric cage to improve visibility and working space. With the substantially symmetrical chamber formed, the double curved tool channels (or alternatively double curved instruments) accommodate for this shaped chamber so as not to sacrifice distances from the target lesion which would otherwise occur if the tips had a single curve.

Figure 15:
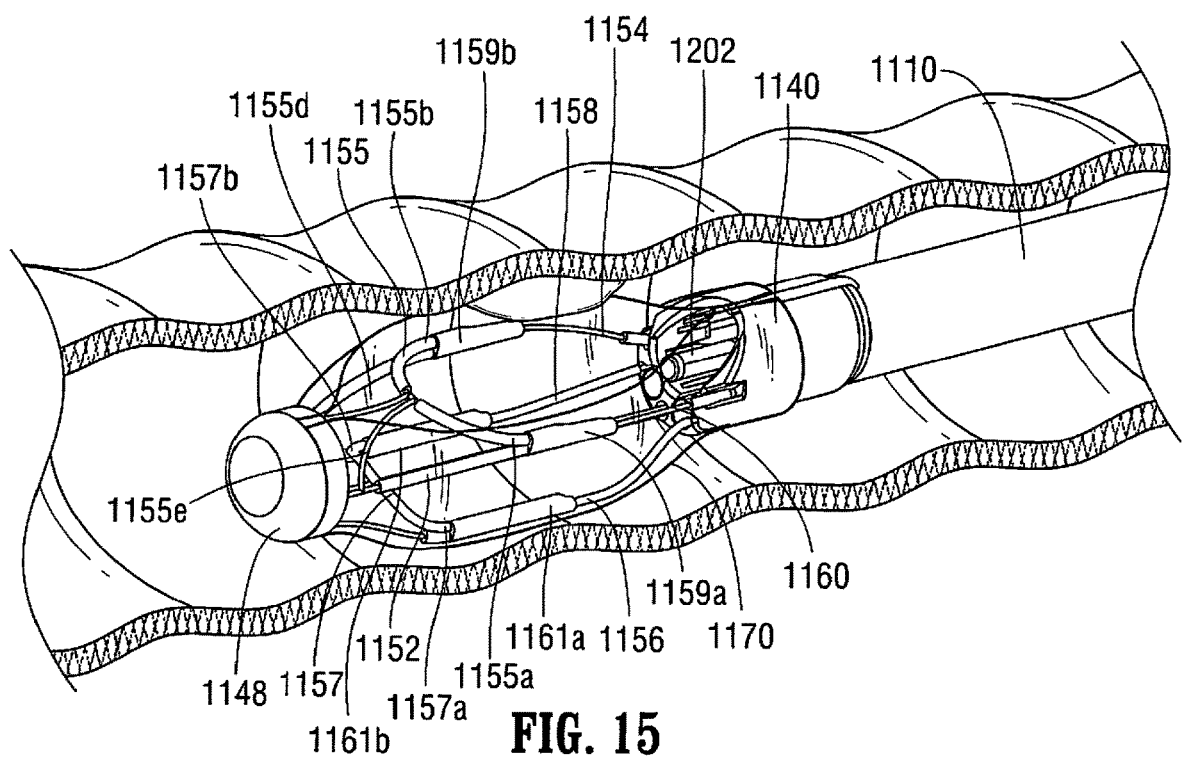
FIG. 15 is a perspective view showing the catheter fully advanced over the endoscope to the desired position adjacent the target tissue, the retractor system shown in the collapsed position.
Figure 21A:
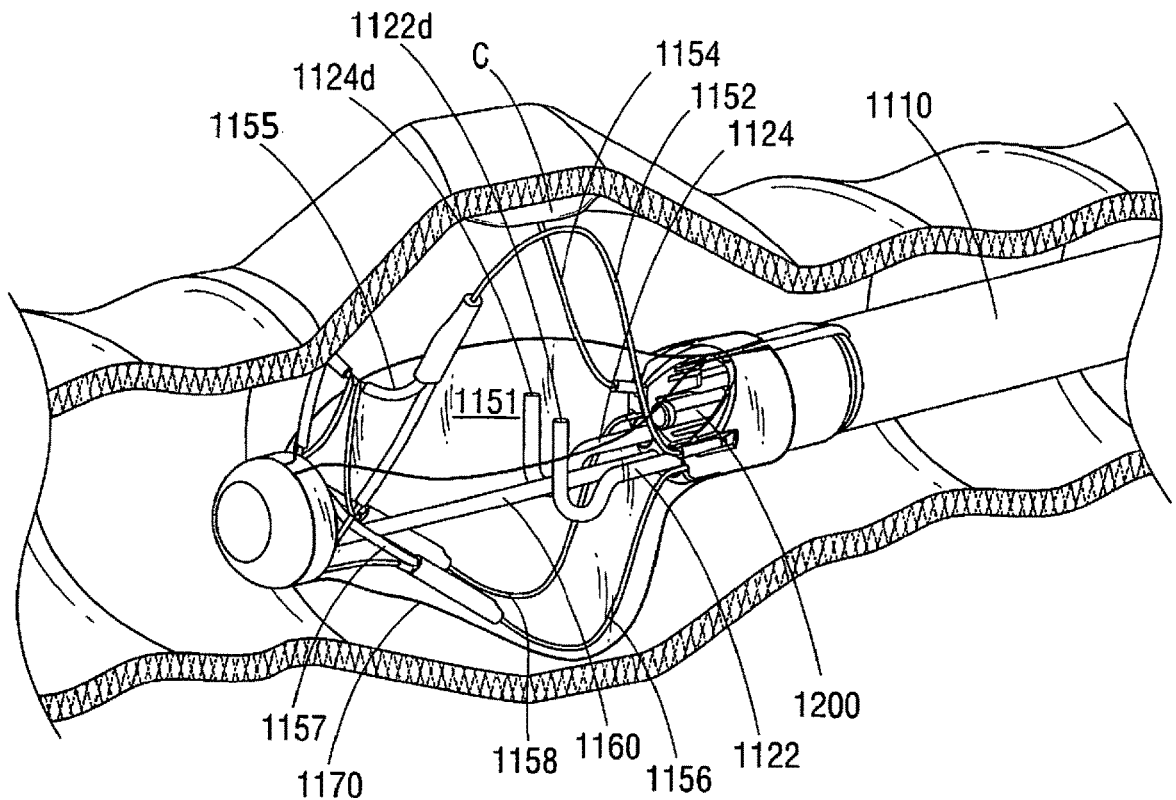
FIG. 21A is a view similar to FIG. 15 showing the retractor system in the expanded position and further illustrating the tool channels being advanced into the working space (chamber) created by the expansion of the retractor system.

As shown by comparing FIGS. 15 and 21A, retractor elements 1152, 1154, 1156, 1158 move from a collapsed insertion position wherein they preferably do not extend beyond the transverse dimension of the catheter 1110 to an expanded position wherein they bow laterally outwardly and have a transverse dimension extending beyond the transverse dimension of the catheter 1110. As shown, the retractor elements 1152, 1154, 1156, and 1158 expand to both sides of a plane passing through the longitudinal axis of the catheter 1110, thereby creating the substantially symmetric cage or working space 1151.

Retractor elements 1152, 1154 have a bridge member 1155 to add stability to the retractor and maintain a desired orientation of the retractor elements during the expansion. The bridge member 1155 is attached to the two retractor elements 1152, 1154, preferably at an intermediate portion, to create a transverse structure for the elements 1152, 1154, limiting side-to side movement. As shown, bridge member 1155 has a first arm 1155a connected to retractor element 1152 and a second arm 1155b attached to retractor element 1154. The upper surface (as viewed in the orientation of FIG. 15) can be arcuate as shown. The bridge member 1155 can be a separate component attached to the retractor elements by tubular elements 1159a, 1159b, which are attached to retractor elements 1152, 1154, respectively. In this version, the tubular element 1159a, 1159b has a first opening to receive the retractor element and a second opening to receive an arm of the bridge member. Note the tubular elements 1159a, 1159b also bulk up the diameter of the retractor elements 1152, 1154 since in some embodiments the retractor elements 1152, 1154 are about 0.035 inches in diameter (although other dimensions are contemplated). Other methods of attachment of the bridge members are also contemplated. Alternately, the bridge member 1155 can be integrally formed with one both of the retractor elements 1152, 1154. The bridge member 1155 can be composed of a material similar to the elements 1152, 1154 or can be composed of a different material. The bridge member 1155 can also include legs 1155d and 1155e which are connected to lower retractor elements 1158, 1156, respectively, to attach the bridge member to lower elements 1158, 1156, respectively, to add to the stability of the retractor system. These leg members are preferably composed of soft elastomeric material such as polyurethane tubing to add more structure to the cage and facilitate expansion of the cage in a more predictable fashion.

Additional bridge members (not shown) can be provided on the retractor elements 1152, 1154 to increase stability. The bridge member 1155 can, in some embodiments, in the collapsed position, extend substantially axially as in FIGS. 15 and 17A, but change to angle inwardly (downwardly) toward the longitudinal axis of the catheter 1110 in the expanded position of the retractor elements 1152, 1154 such as in FIG. 21A.

An additional bridge member 1157 (or alternatively multiple bridge members) extends between the two lower (as viewed in orientation of FIG. 15) retractor elements 1156, 1158. These elements 1156, 1158 can help open up the lower section of the retractor system 1150, and help form the cage for the working space, and the bridge member(s) 1157 can help to stabilize these elements 1156, 1158, e.g., limit side to side movement. The bridge member 1157 as shown has arms 1157a, 1157b connecting to elements 1156, 1158, respectively. The bridge member 1157 can be a separate component attached to the retractor elements by tubular elements 1161a, 1161b which are attached to retractor elements 1156, 1158, respectively. The tubular elements 1161a, 1161b can have a first opening to receive the element 1156 or 1158 and a second opening to receive an arm of the bridge member 1157. Other ways of attaching the bridge member(s) are also contemplated. Alternatively, the bridge member 1157 can be integrally formed with one or both of the retractor elements 1156, 1158. The bridge member 1157 can be composed of a material similar to the elements 1156, 1158 or can be composed of a different material.

Additional bridge members (not shown) can be provided on the retractor elements 1156, 1158 to increase stability. The bridge member 1157 can, in some embodiments, in the collapsed position, be substantially parallel with a longitudinal axis of the catheter 1110 or extend substantially axially such as in FIG. 15 and change to an angular position in the expanded position of the retractor elements.

The catheter 1110 includes a proximal coupler (cap) 1140 through which the retractor elements extend. Handle housing 1130 includes a longitudinally extending slot 1131 (FIG. 16) along which retractor actuator 1132 axially slides. The retractor elements 1152, 1154, 1156, and 1158 are coupled to the actuator 1132 via block 1146, shown in FIGS. 20A and 20B. That is, each retractor element 1152, 1154, 1156, 1158 has a proximal extension that extends through the respective lumen in the catheter 1150 and is connected at its proximal end to the block 1146. In this manner, when the actuator 1132 is moved along axial slot 1131 from its proximal position of FIG. 20A to its distal position of FIG. 20B, the block 1146 is moved distally, thereby forcing the retractor elements 1152, 1154, 1156, 1158 laterally outwardly since the elements 1152, 1154, 1156, 1158 are fixedly attached to the distal coupler 1148 at their distal ends. In one embodiment, the elements 1152, 1154, 1156 and 1158 can be fixed within slots formed in the distal coupler 1148. Note the proximal and distal couplers 1140, 1148 can have openings dimensioned to receive an endoscope when the catheter 1110 is backloaded over the endoscope as described below. Housing 1130 can include a plurality of teeth (not shown) for engagement by a tooth coupled to the actuator 1132, thereby forming a retaining or locking mechanism to retain the retractor elements in one of several select positions. A release mechanism for the retaining or locking mechanism can be provided.

Additionally, it should be appreciated that alternative ways to expand the retractor elements can be utilized, including for example providing relatively movable couplers 1140, 1148 to expand the retractor elements 1152, 1154, 1156, 1158 in the same manner as the couplers described above, e.g., couplers 198, 199. The retractor elements can also alternatively be made of self-expanding material, such as shape memory material, which expand when exposed from the catheter or sheath.

Retractor elements 1152, 1154, 1156, and/or 1158 can optionally have a small crimp forming a flattened position at a distal end adjacent where they are anchored to the distal coupler 1148. This reduces the bending stiffness at the point so it acts like a hinge to create a more predictable direction of expansion, e.g., to deflect upwardly (or downwardly) and slightly outwardly. This also decreases the amount of force required to initiate the bending. Such flattened portion can also be used with the retractor elements of the other embodiments disclosed herein.

The retractor system 1150 can be configured to reversibly stiffen an otherwise flexible arrangement of the retractor

1150. In this regard, retractor system 1150 can include a substantially-rigid beam to support the expanded retractor 1150 which helps to create a more stabilized chamber (or cage) as described herein. With reference to FIGS. 15 and 17A, a flexible tube or beam 1160 is provided in the collapsed configuration, whereas in FIG. 17B, the retractor system has a rigid beam that is formed from the flexible beam 1160. More specifically, in this embodiment, the flexible beam 1160 is in the form of a rod or tube 1165 having a lumen to slidably receive a stabilizing or rigidifying structure such as a rigid tube or rod (beam) 1162. The rigidifying (stabilizing) structure 1162 is independently actuated by the user by movement of actuator 1134. Actuator 1134 is slidably mounted within a longitudinally extending slot of housing 1130. In the initial position of FIG. 17A, rigidifying structure 1162 is retracted within a lumen of the catheter and either not engaged, or only partially engaged, with flexible tube (or rod) 1160. Rigidifying structure 1162 is attached at is proximal end to sliding block 1164 which is operably connected to actuator 1134. To rigidify tube 1160, actuator 1134 is slid distally to the position of FIG. 17B, thereby advancing sliding block 1164 and the attached stabilizing structure 1162 distally. Such movement advances the rigidifying structure 1162 through the lumen 1165 of the flexible tube 1160 to the distal end 1160a to thereby stiffen the beam. The rigidifying structure 1162 can optionally be removed from the flexible beam 1060 to return the system back to the original more flexible state to aid collapsing of the retractor system 1050 by sliding the actuator 1134 in the reverse direction (proximally) within the axial slot, thereby withdrawing rigidifying structure 1162 from the advanced position within flexible tube 1160. In one embodiment, the rigidifying structure 1164 is in the form of a structure having a proximal and distal metal tubular structure joined by a flexible braid polyimide tube. However, it should be appreciated that other structures are also contemplated. Note the structures 1160, 1162 can be substantially circular in cross-section, although other cross-sectional shapes are also contemplated. The rigid beam limits deflection of the distal end 1111 of the catheter 1110 which could otherwise occur by pressure exerted on the distal end by the body lumen wall.

As shown in FIGS. 17A and 17B, the actuator can include a connector 1135 having a tooth or pawl 1137 to engage a tooth on the rack 1138 positioned within housing 1130 to retain the rigidifying structure 1164 in one of several selected positions.

Figure 17C:
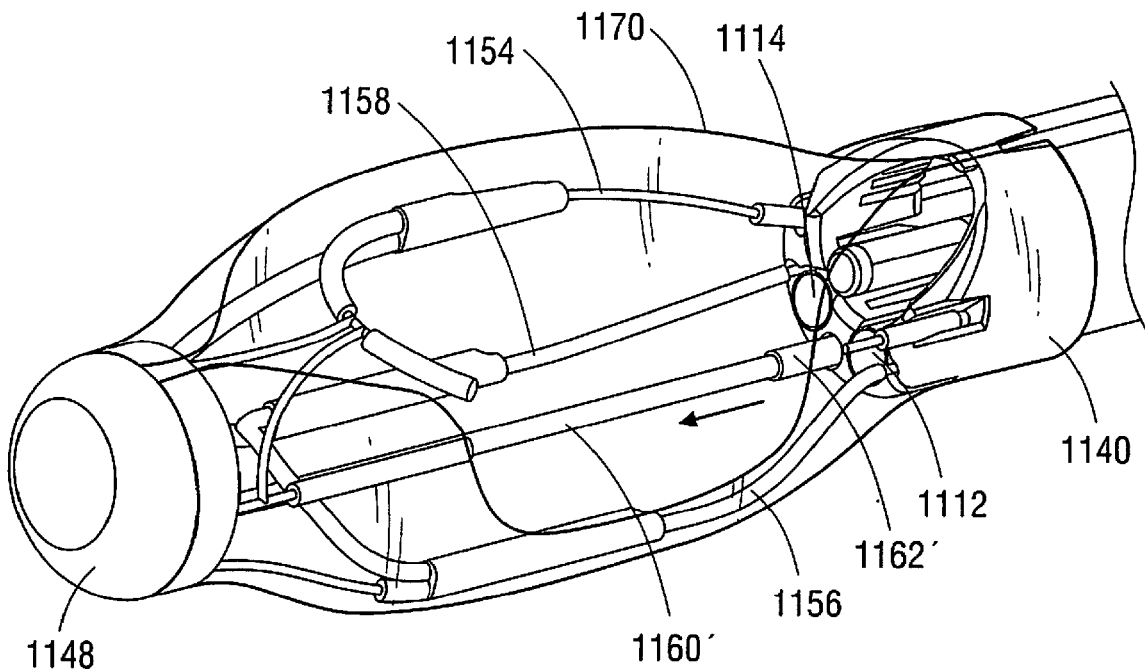
FIG. 17C is a perspective view similar to FIG. 15 showing an alternate embodiment of the rigidifying structure.
Figure 17D:
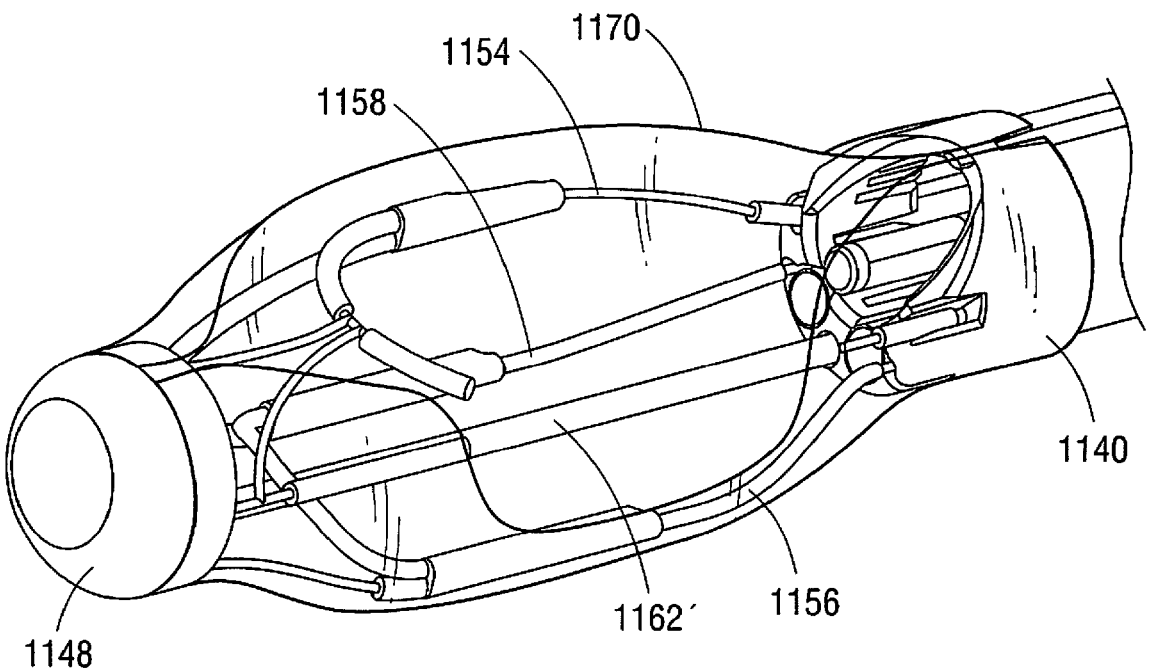
FIG. 17D is a perspective view similar to FIG. 17C showing the rigidifying structure of FIG. 17C advanced over the flexible element.

In the alternate embodiment of FIGS. 17C and 17D, instead of advancing a rigidifying structure within the lumen of the flexible element, the rigidifying structure is advanced over the flexible element. More specifically, flexible beam 1160' is rigidified by movement of a rigidifying structure, e.g., tubular member 1162', over the flexible beam 1160'. That is, rigidifying member 1162' has a lumen configured and dimensioned to receive flexible beam 1160' as it is passed thereover in the direction of the arrow of FIG. 17C. Note that flexible element 1152 has been removed from FIGS. 17C and 17D for clarity. Actuator 1134, as well as alternative methods, can be utilized for such movement In the alternative embodiment of FIG. 26A, the retractor system does not include a rigidifying structure. In all other aspects, the retractor system 1350, having retractor elements 1352, 1354, 1356 and 1358, is the same as retractor system 1150.

A covering or cover 1170 is preferably provided at a distal end of the catheter 1110. Covering 1170 in the illustrated embodiment is mounted around the perimeter of the proximal coupler 1140 and the distal coupler 1148. In some embodiments, the cover 1170 is pleated and sealed around the couplers (caps) 1140, 1148 by a heat shrink wrap. The cover 1170 is positioned around the elements 1152, 1154, 1156, 1158 in the collapsed insertion position, with an opening in the cover 1170 facing toward the target tissue, e.g., the lesion to be removed. That is, in the orientation of FIG. 15, the opening in cover 1170 faces upwardly. The cover 1170 can be configured to have an opening in the collapsed position, or, alternatively, it can provided with a slit which can be opened due to stretching when the retractor elements 1152, 1154, 1156, and 1158 are moved to the expanded position. When the retractor elements 1152, 1154 are expanded, they move past the cover 1170 toward the target tissue. Alternatively, the edges of the cover 1170 can be attached to the retractor elements 1152, 1154, 1156, and 1158 thereby move with the retractor elements. When the target tissue is removed by the endoscopic instruments described herein, the removed tissue is placed within the cover 1170, and the cover 1170 is closed, e.g., by a suture or string 1172 shown in FIG. 29 to encapsulate the tissue and prevent leakage and seeding during removal from the body lumen. The suture 1172 can be embedded in a wall of the cover 1170 or in pockets or channels formed in the cover 1170, where it is permanently fixed at a distal anchor point, and pulled proximally to tension the suture 1172 and close the cover 1170.

The cover 1170 by covering the retractor elements 1152, 1154, 1156, 1158 can provide a smooth and atraumatic surface for the delivery of the retractor system to the target site. The cover 1170 also helps to prevent unwanted tissue, e.g. the luminal walls, from entering through the spaces between the beam 1160 and retractor elements during the surgical procedure.

In a preferred embodiment, the two ends of suture 1172 extend out of tubing 1139 (FIG. 11). Their proximal ends can be covered by a length of tubing to facilitate grasping by the user. The suture 1172 extends through switch 1137 and tubing 1139, through a dedicated lumen (channel) in the catheter, through the covering 1170, and is looped at the distal cap (coupler) 1148 where it is attached (anchored). During the procedure, the suture 1172 remains untensioned. After the tissue is placed within the cover (bag) 1170, the two proximal ends of the looped suture 1172 are pulled proximally to tension the suture 1172 to close the cover 1170. The switch can then be moved to frictionally engage the suture 1172 to secure it so it locks in the tensioned position to maintain closure of the cover 1170.

The use of the system of FIG. 11 will now be described with reference to removing a lesion, such as a polyp, from a colon wall, it being understood, however, that the system 1100 can used for other procedures within the colon or the gastrointestinal tract, as well as used for other procedures in other body lumens or body spaces of a patient.

Figure 13:
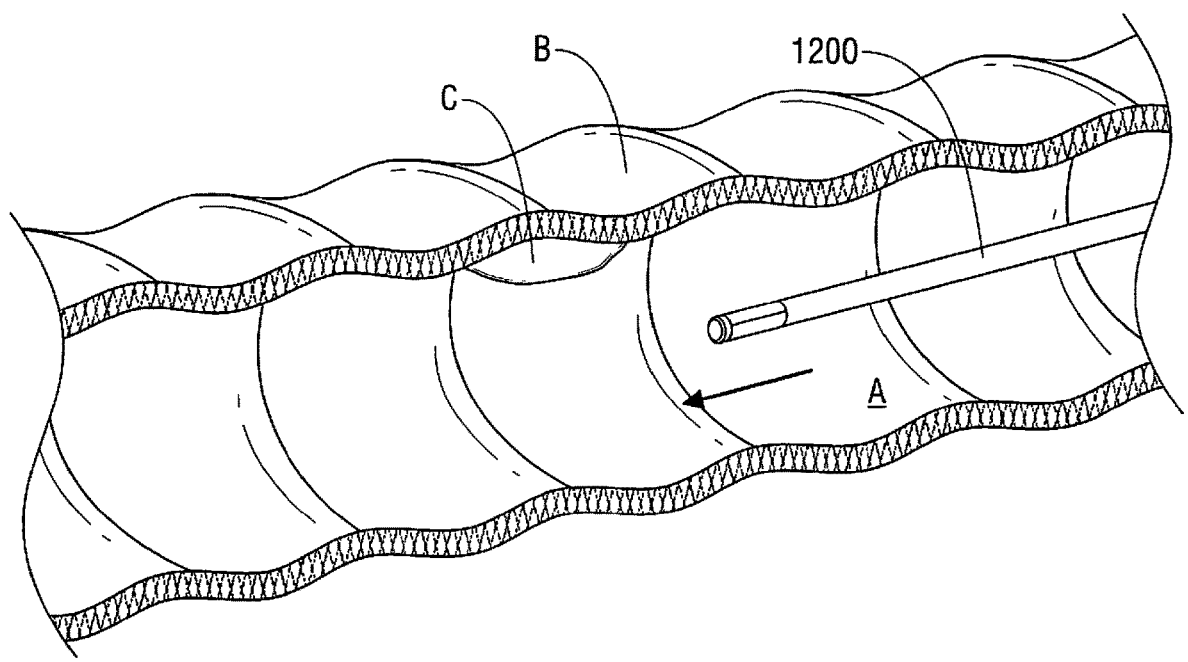
FIG. 13 illustrates insertion of the endoscope through the colon.
Figure 14:
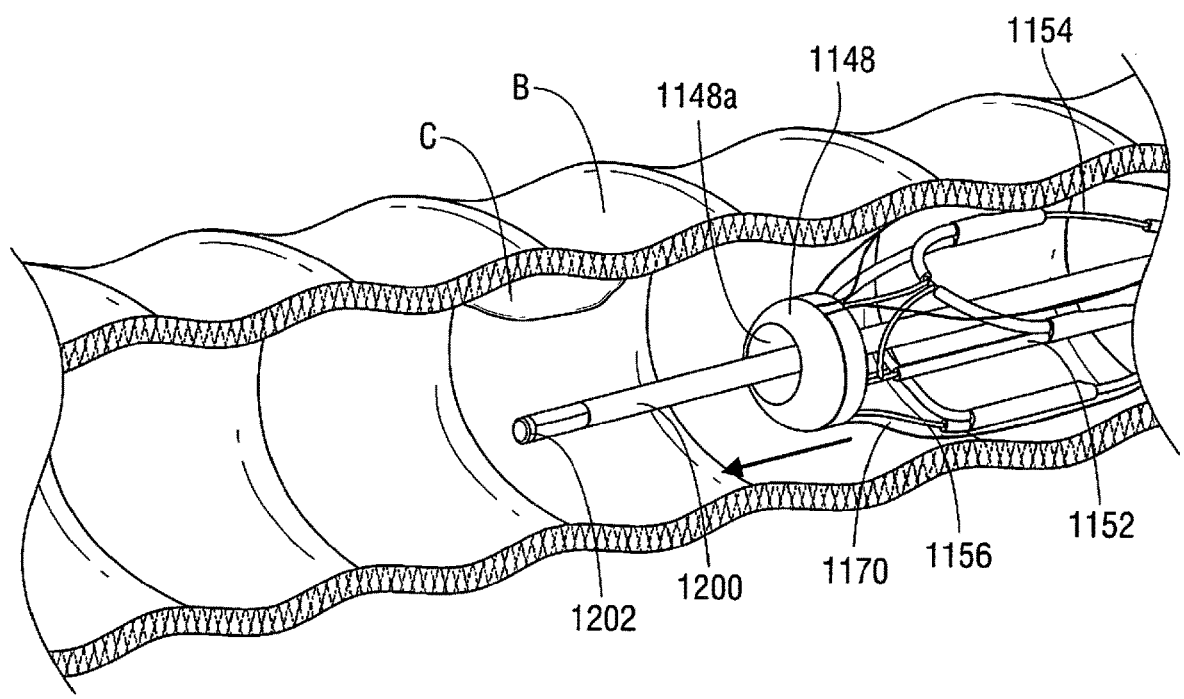
FIG. 14 is a perspective view showing the catheter of FIG. 11 being further advanced over the endoscope of FIG. 13, the retractor system shown in the collapsed position.

Turning first to FIGS. 12 and 13, a distal viewing endoscope 1200, in which the system 1100 has been backloaded over the proximal end 1201, is inserted through lumen A in the colon B in a procedure to remove the target polyp C from the wall of the colon B. The endoscope 1200 in this embodiment is a distal viewing scope with a wide distal viewing area of about 150-170 degree range so the polyp C and surrounding area can be visualized. After placement of the scope 1200 adjacent the target issue, i.e., slightly proximal of the target polyp C, the system 1100 is further advanced over the endoscope 1200. Distal coupler (cap) 1148 has an opening 1148a, and proximal coupler (cap) 1140 has an opening communicating with the lumen 1116 (FIG. 16) of the catheter 1110 to enable such backloading of the endoscope 1200 and advancement of the system 1100 thereover. The catheter 1110 is advanced over the endoscope 1200 as shown in FIG. 14 until it reaches the target site as shown in FIG. 15, with the retractor system 1150 aligned with the polyp C. As can be appreciated, in this insertion position of the catheter 1110, the retractor system 1150 is in the non-expanded (or collapsed) position, with retractor elements 1152, 1154, 1156, 1158 preferably not exceeding, or only slightly exceeding, the transverse dimension of the catheter 1110. In this position, the retractor elements are covered by the covering 1170. As shown, in this position, the distal end 1202 of the endoscope 1200 is preferably positioned at the end of proximal coupler 1140 and does not extend into the working space 1151 to thereby leave more room for maneuvering of the endoscopic instruments within the working space. Other positions, however, are also contemplated, e.g., in some versions the endoscope can extend into the working space 1151. Note also in this insertion position, actuators 1134 and 1132 are in their retracted position as shown in FIG. 16.

Next, to rigidify the retractor system 1150, the actuator 1134 is moved distally from the position of FIG. 17A to the position of FIG. 17B (see also the arrow in FIG. 16) to advance rigidifying structure 1162 from the retracted position to an advanced position within lumen 1165 of flexible tube 1160. This stiffens/stabilizes the retractor system 1150 as discussed above. Note, as discussed above, the retractor system 1150 can alternatively be stiffened/stabilized by advancement of a rigidifying structure over the flexible element as shown in FIGS. 17C and 17D. Also note that if the retractor system does not include a stiffening/stabilizing structure such as in the embodiment of FIG. 26A, an actuator is not provided and this step is skipped.

The retractor system 1150 is now expanded. Actuator 1132 is advanced distally from the position of FIG. 20A to the position of FIG. 20B (see also FIG. 19). This advances block 1146 (which is operably coupled to retractor elements 1152, 1154, 1156, and 1158 as discussed above) which forces retractor elements 1152, 1154, 1156 and 1158 laterally outwardly to the position of FIG. 20B, thereby creating the substantially symmetric working space (chamber).

Figure 21B:
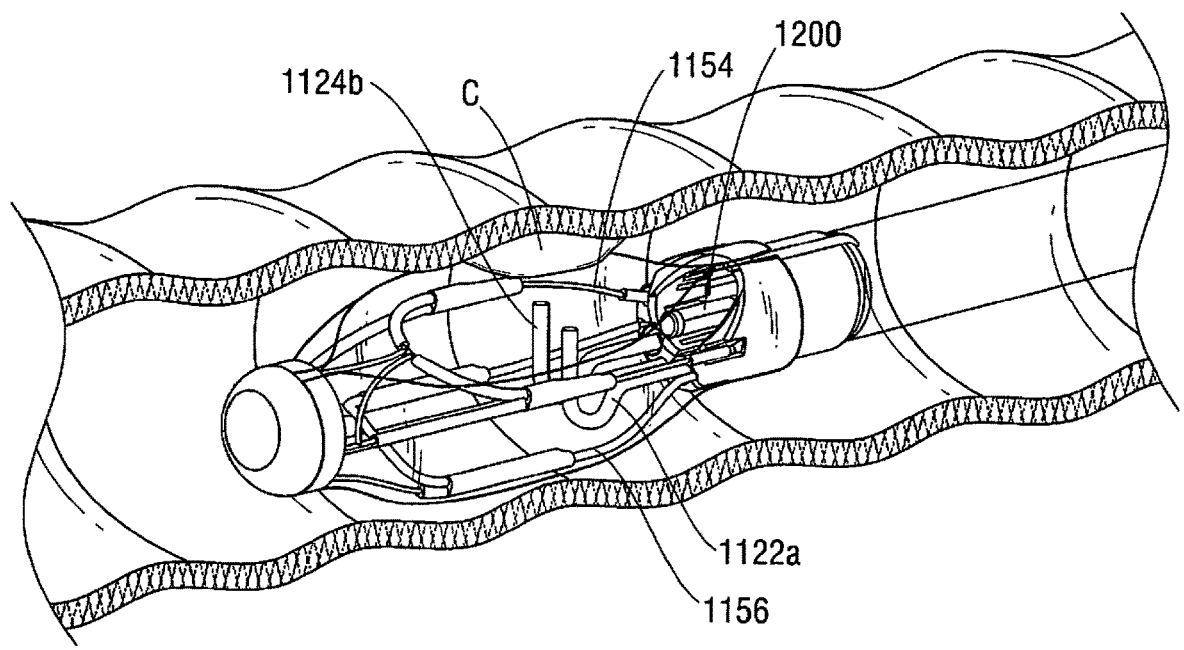
FIG. 21B is a view similar to FIG. 21A illustrating an alternate embodiment wherein the tool channels are advanced from the catheter prior to expansion of the retractor system.

Next, tool channels 1122, 1124 are inserted through the ports 1115, 1117 in the proximal region of the catheter 1110 (see FIG. 19A) and advanced by the user through the catheter lumens 1112, 1114 so they extend out the distal openings of the lumens 1112, 1114 and into the chamber 1151 as shown in FIG. 21A. Note as they emerge from the lumens 1112, 114, and out of the confines of the lumen walls of the catheter 1110, their distal tips 1122*a*, 1124*a* return to their double curved (double bent) position, curving downwardly, then upwardly (as viewed in the orientation of FIG. 21A) toward the polyp C. Note in FIG. 21A, the retractor elements are first expanded, followed by insertion of the tool channels 1122, 1124 out of the catheter lumens 1112, 1114 and into the working space 1151. However, it is also contemplated that in an alternative embodiment, the tool channels 1122, 1124 can be inserted through the catheter lumens 1112, 1114 and into the working space 1151 prior to expansion of the retractor elements 1152, 1154. This alternate method is shown in FIG. 21B, with the tool channel tips 1122*a*, 1122*b* exposed, but the retractor system 1150 still in the non-expanded position. Note the tool channels 1122, 1124 can be independently rotated and/or moved axially to adjust their position with respect to the polyp C. As can be appreciated, the terms upwardly and downwardly as used herein refer to the orientation of the system in the referenced Figures. If the position of the system (and target tissue) changes, the orientation and terms would also change.

Figure 19A:
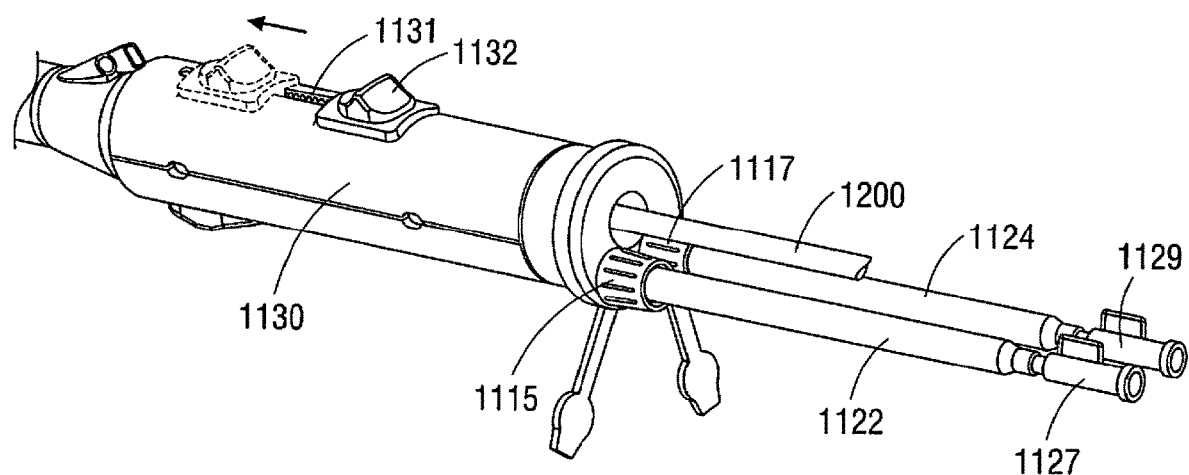
FIG. 19A is a perspective view illustrating the tool channels inserted into the catheter of FIG. 11
Figure 19B:
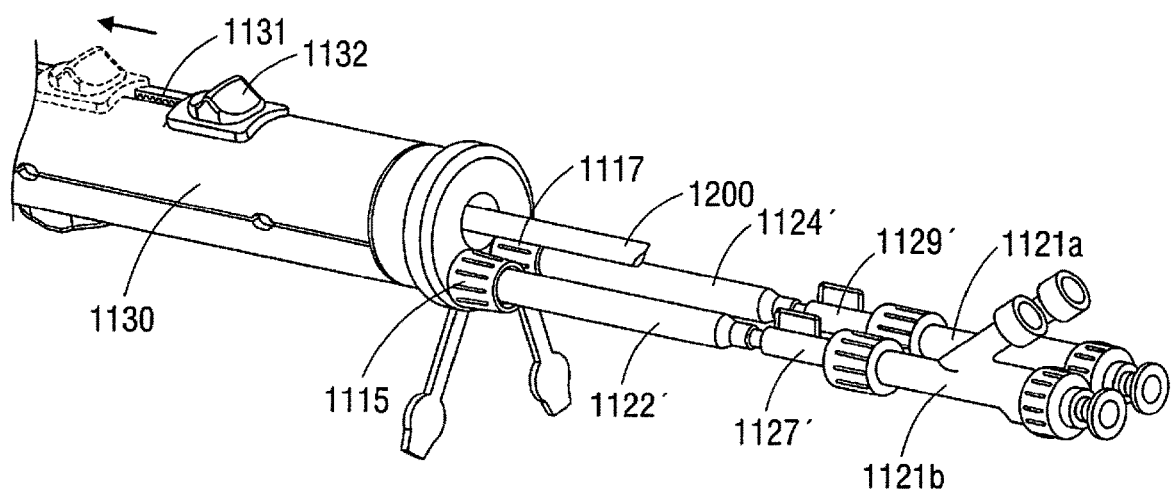
FIG. 19B is a perspective view similar to FIG. 19A illustrating an alternative embodiment of the tool channels.
Figure 20A:
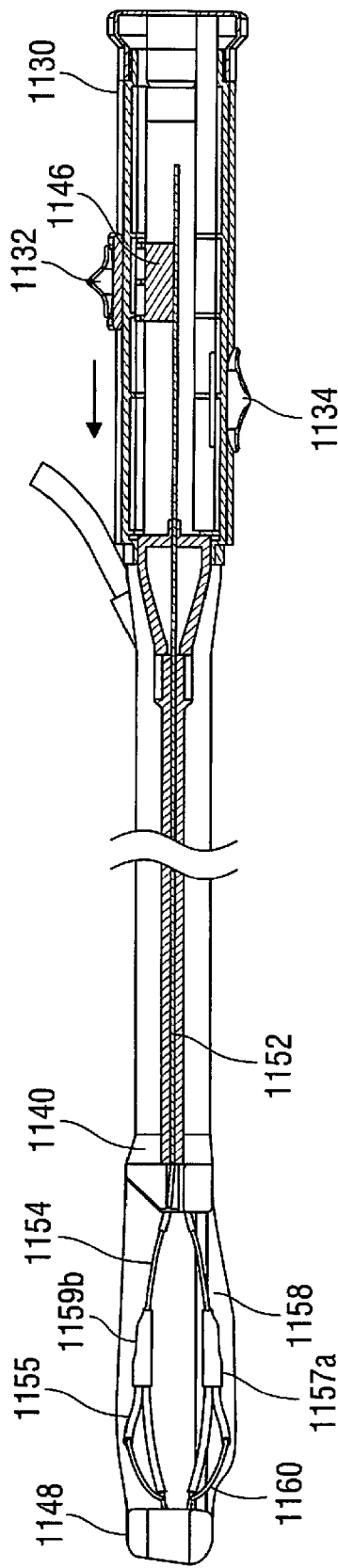
FIGS. 20A and 20B are side cross-sectional views showing movement of the actuator from a proximal position to a distal position to move the retractor system from the collapsed to the expanded position.
Figure 20B:
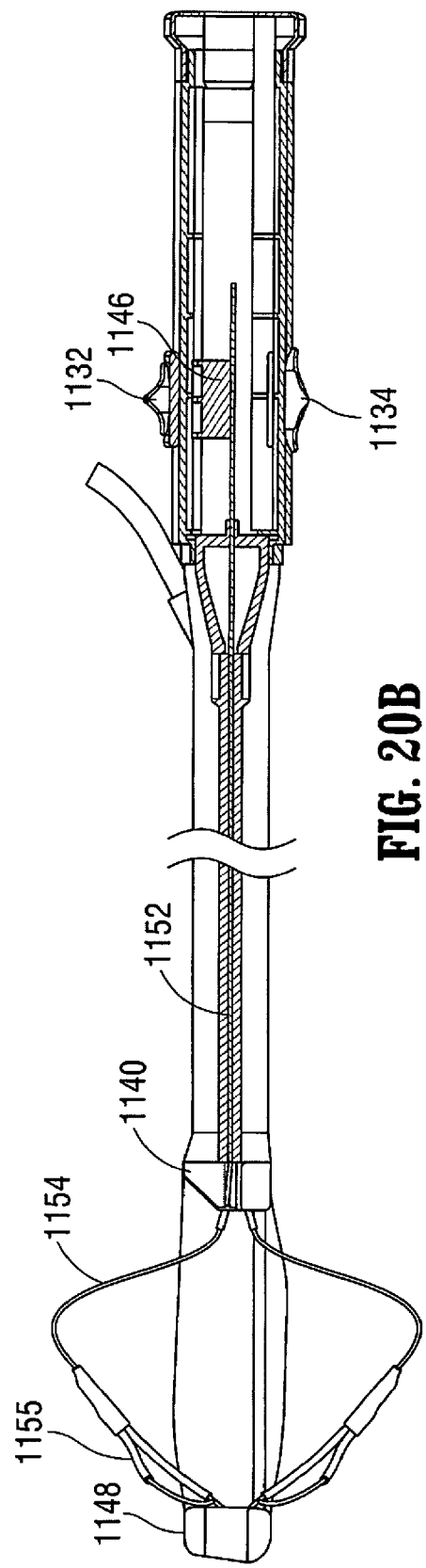
Figure 22:
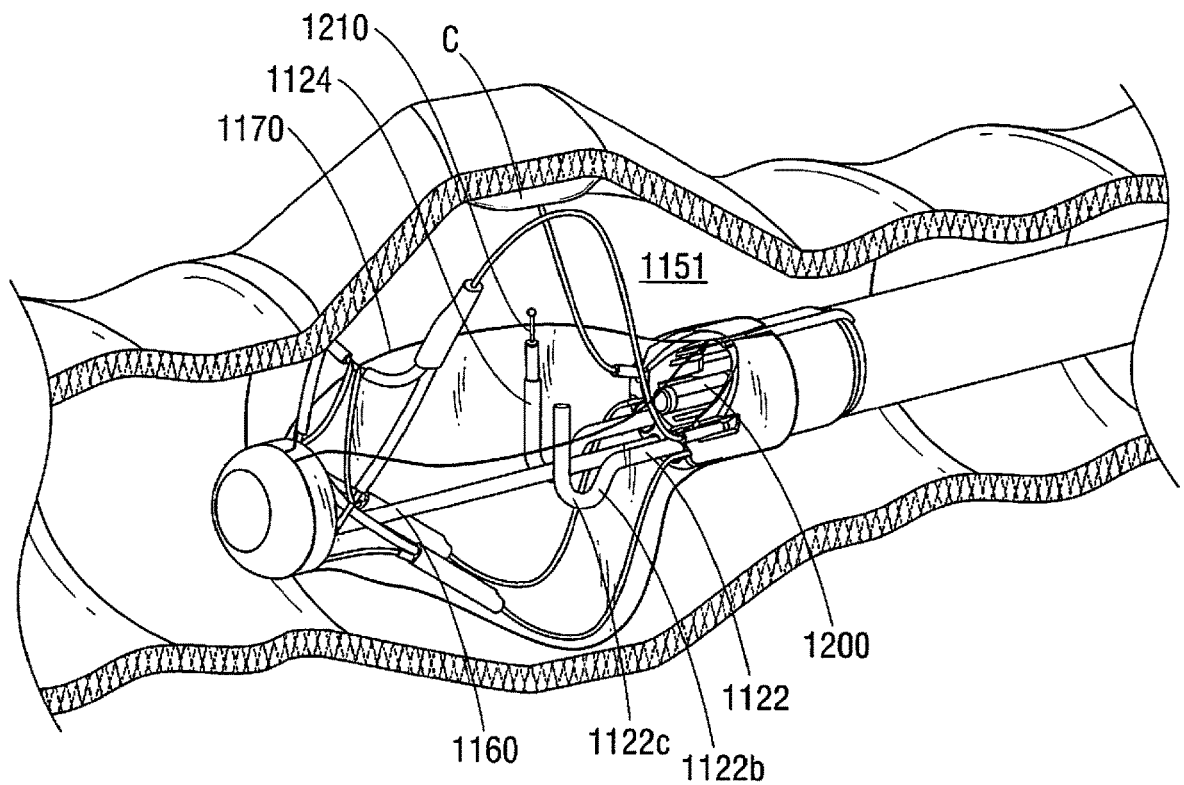
FIG. 22 is a view similar to FIG. 21A showing a first endoscopic instrument (tool) advanced from a first tool channel.
Figure 23:
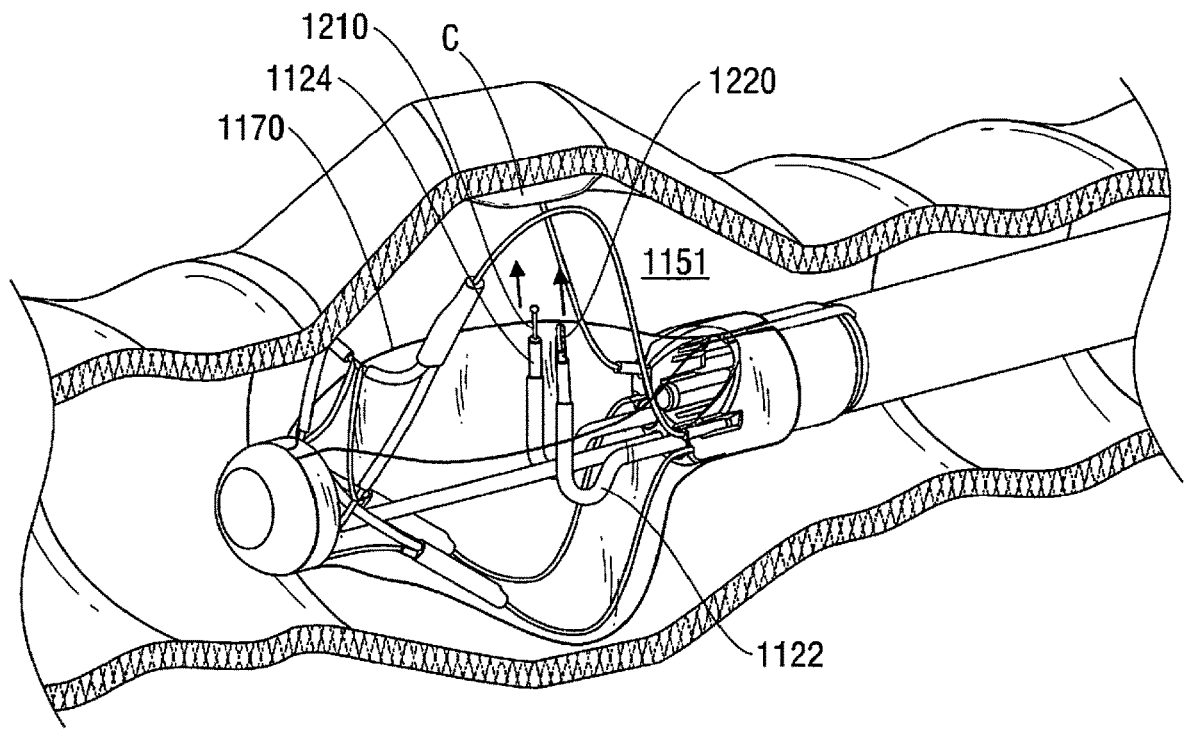
FIG. 23 is a view similar to FIG. 22 showing a second endoscopic instrument (tool) advanced from a second tool channel.
Figure 24:
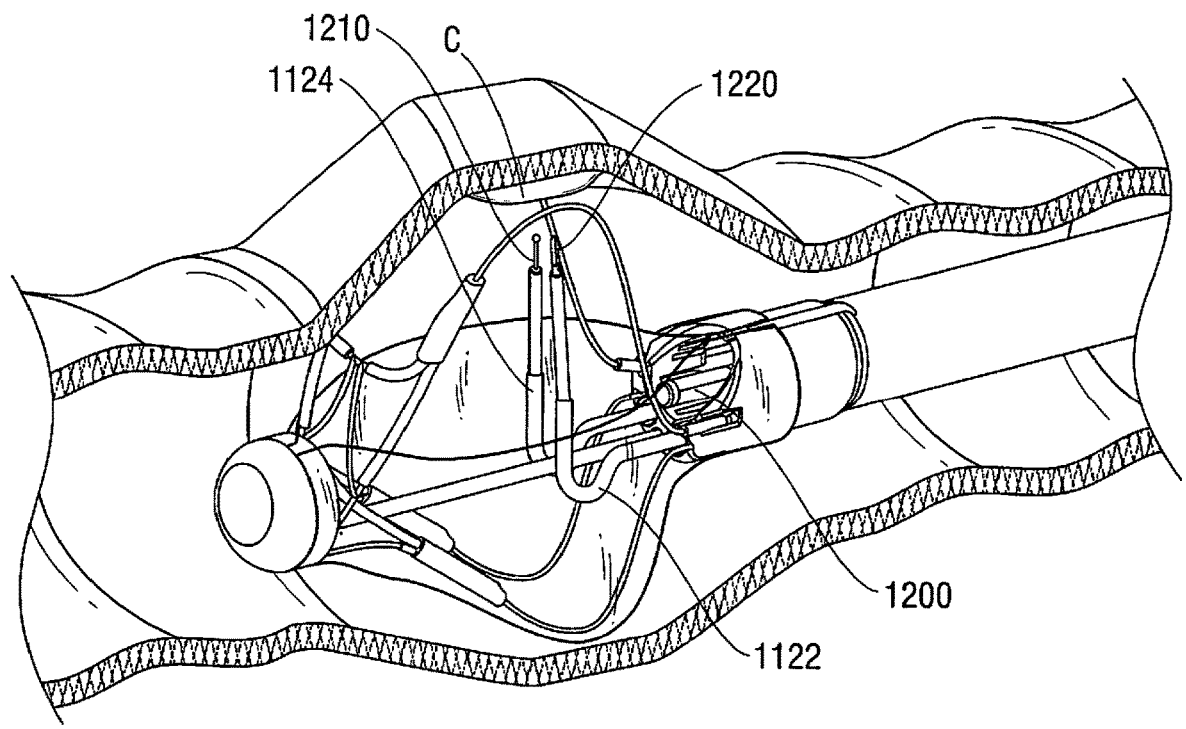
FIG. 24 is a view similar to FIG. 23 showing both endoscopic instruments further advanced from the tool channels.
Figure 25:
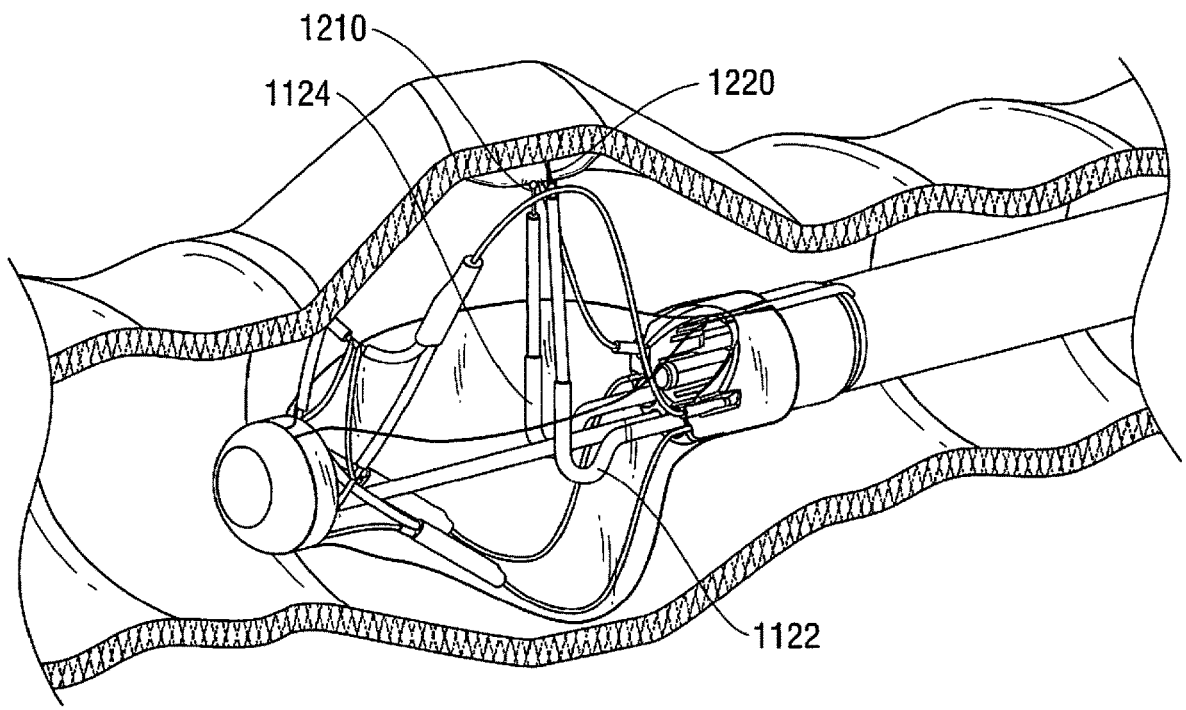
FIG. 25 is a view similar to FIG. 24 showing the endoscopic instruments further advanced from the tool channels to dissect the lesion on the colon wall.

After insertion of the tool channels 1122, 1124, endoscopic instrument (tool) 1210 is inserted through the luer fitting 1129 (FIG. 19A) of the tool channel 1124 and advanced through the lumen (channel) of the tool channel. As shown in FIG. 22, a first endoscopic instrument 1210 extends from tool channel 1124 and follows the double curve of the tool channel 1124. A second endoscopic instrument (tool) 1220 is inserted through the luer fitting 1127 of tool channel 1122 and advanced through the lumen of the tool channel 1122. As shown in FIG. 23, the second endoscopic instrument follows the double curve of the tool channel 1122. As noted above, the tool channels can include a valve, such as the hemostatic valves as shown in FIG. 19B, so insufflation is not lost during insertion and removal of the endoscopic instruments from the tool channels. The endoscopic instruments 1210, 1220 can be moved further axially as shown in FIGS. 24 and 25 to extend further from the tool channels 1122, 1124 to contact and treat, e.g., remove, the polyp C. This movement of the endoscopic instruments shown by comparing FIGS. 23-25 shows the advantage of the tool channels 1122, 1124. As can be seen, once the tool channels 1122, 1124 are in the desired position with respect to the polyp C, they can be considered as defining a fixed curve, the fixed curve being the second curve 1122*c* and 1124*c*. This means that when the endoscopic instruments 1210, 1220 are axially advanced, they move closer to the target polyp C, without a change in curvature and without a change in their axial position with respect to the polyp C, thus providing an extra degree of freedom. The endoscopic instrument 1210, which in the illustrated embodiment is a grasper, applies tension on the polyp C while the electrosurgical dissector 1220 dissects/severs the polyp C from the colon wall B. Other endoscopic instruments for polyp removal can also be utilized. Additionally, in some embodiments, a single tool channel can be utilized and another endoscopic instrument, e.g., a grasper or a dissector, can be inserted through a working channel (lumen) of the endoscope. Such instrumentation inserted through an endoscope can also be utilized with the embodiments having two or more tool channels.

Figure 30:
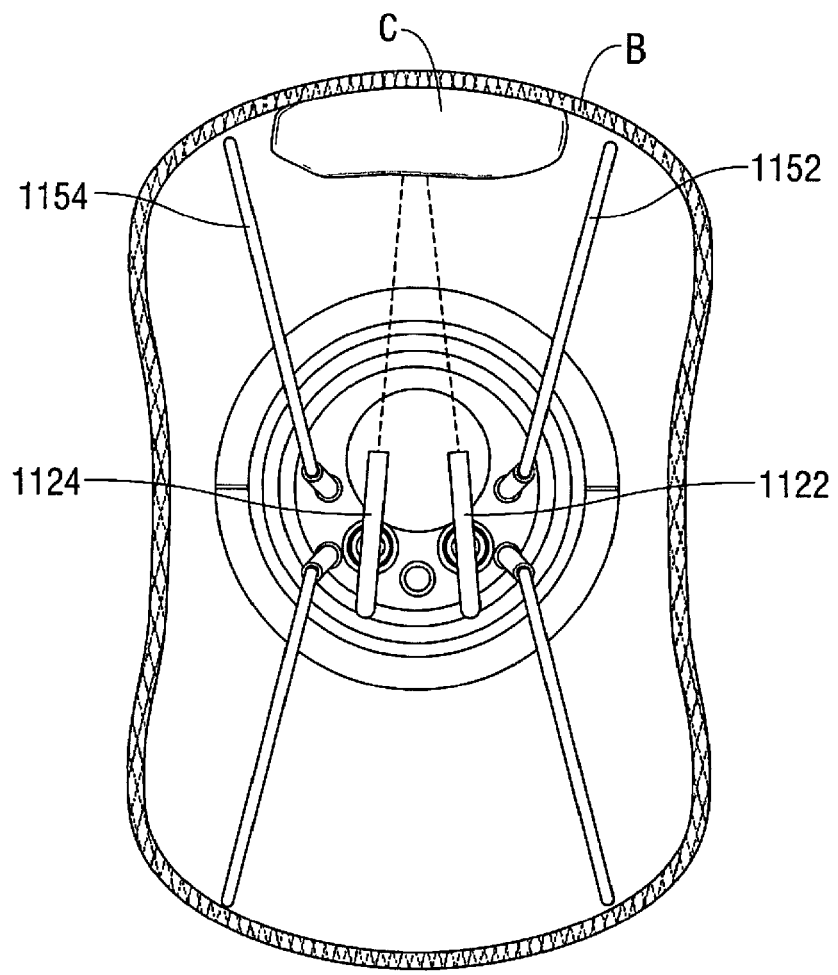
FIG. 30 is a front view of the system in the expanded position of the retractor system and showing two channels extending from the catheter.

Also note that due to the angles of the tool channels 1122, 1124 and thus the endoscopic instruments inserted therethrough, tissue triangulation can be achieved as depicted by the dotted lines in FIG. 30. Also as discussed above, the double curve (somewhat U-shaped tip) increases the distance of the distal openings in the tool channels 1122, 1124 from the target tissue as compared to a tool channel with a single curve. This is especially advantageous when used with a substantially symmetric chamber which cannot form the same space as the asymmetric chamber described in the U.S. application Ser. No. 13/913,466 noted above as the colon or body lumen has a maximum expansion before it is overstretched or damaged. In the asymmetric expansion, reshaping can occur with an increased distance for the working instruments from the lesion and increased working space. With the substantially symmetric chamber, the distance for the working instruments from the lesion would be reduced compared to the asymmetric chamber if not for the double curve provided by the present invention. Maintaining this comparable increased distance can be appreciated by comparing FIGS. 6 and 10A as discussed above, and further by the shorter distal length of FIG. 18A. Stated another way, the asymmetric chamber of FIGS. 9 and 10A reconfigures the lumen to increase and optimize the working space around the target tissue (as it creates more space around the tissue) and increases the distance between the target tissue and opposite wall. In the symmetric chamber of the present invention, a non-working space is expanded at the expense of the working space near the target tissue. Thus, the distance between the target tissue and longitudinal axis of the catheter is decreased. To compensate for this decrease, the distance from the target tissue to the tool guides (channels) is increased by the double bent tip, achieving the objective of positioning the distal opening in the tool guides as far away from the target tissue as possible. Thus, the first bend increases the distance from the distal opening of the tool guide from the target tissue. The second bend directs the distal opening toward the target lesion.

Figure 26:
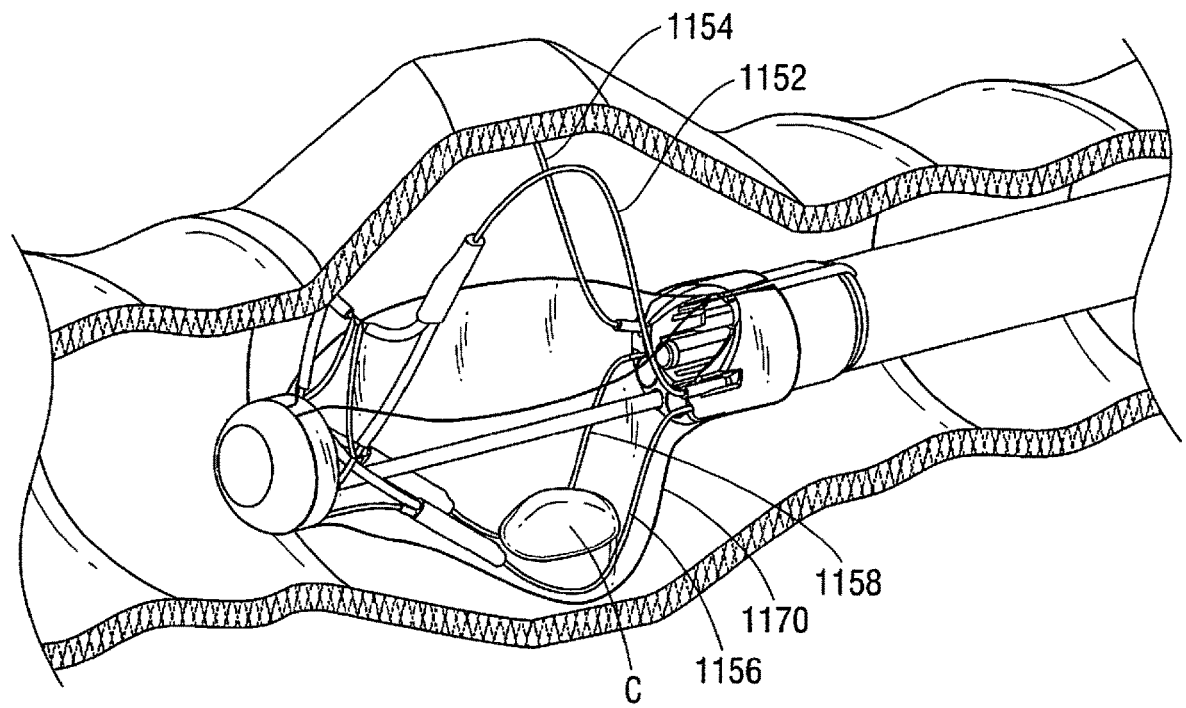
FIG. 26 is a view similar to FIG. 25 showing the lesion which has been removed from the colon wall by the dissecting instrument placed within the retractor system and FIG. 26A is a view similar to FIG. 26 showing an alternate embodiment without a rigidifying structure.
Figure 26A:
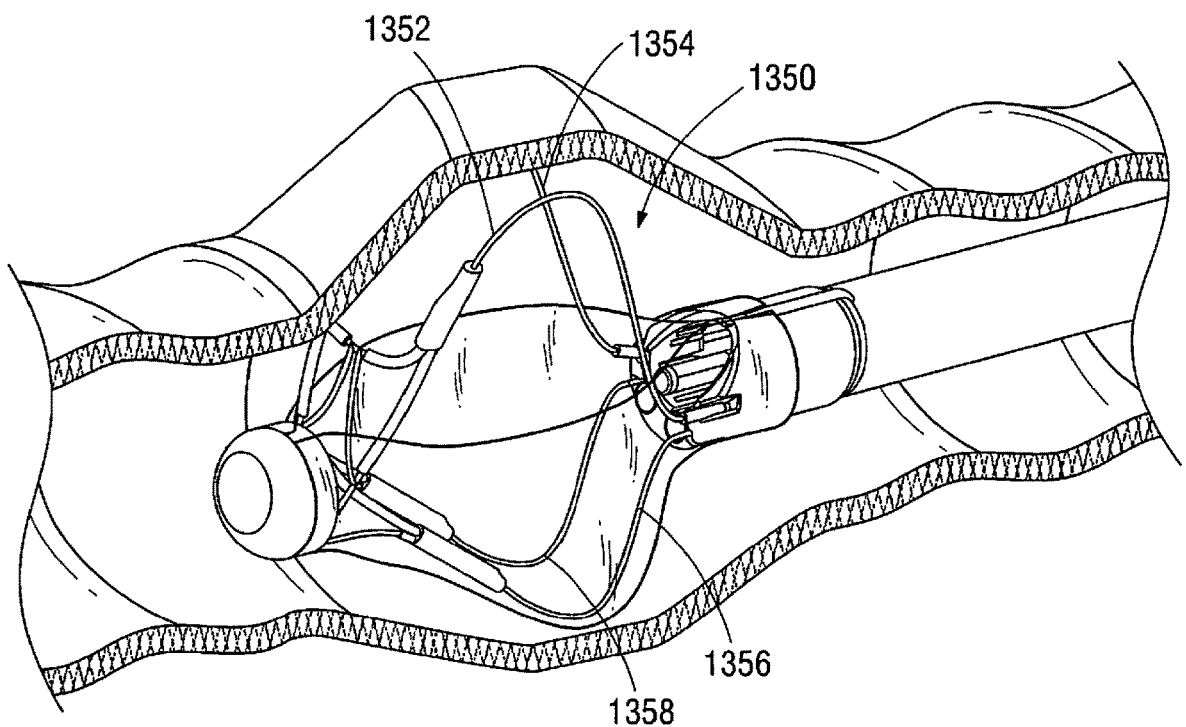
Figure 27:
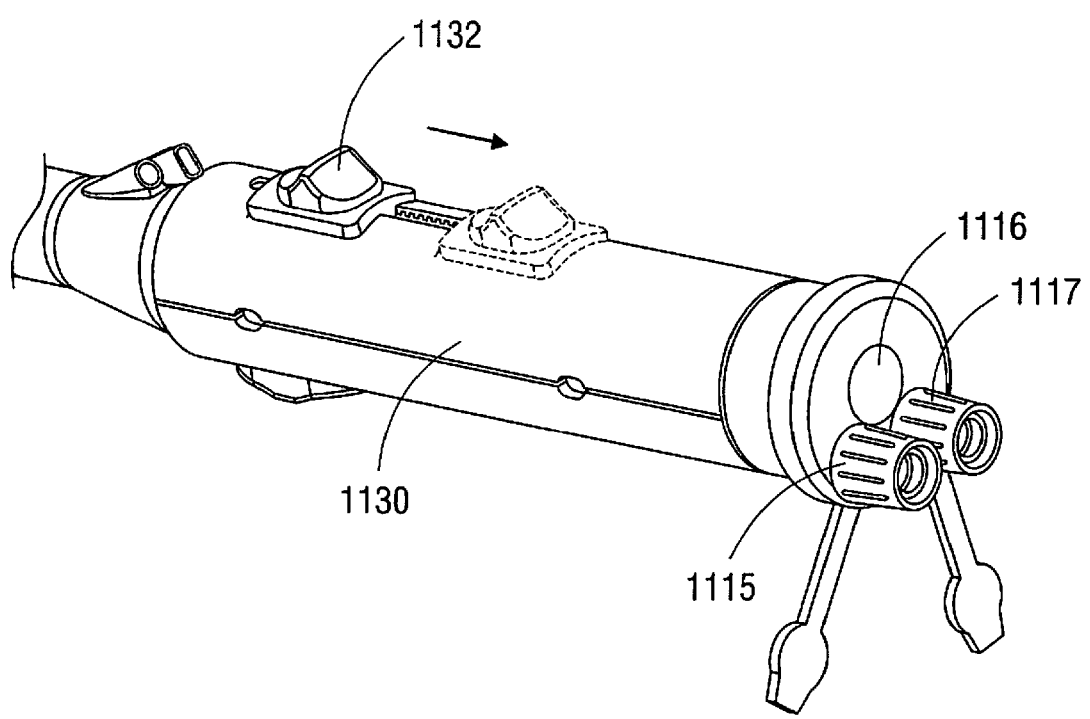
FIG. 27 is a perspective view of the proximal end of the catheter showing proximal movement of the actuator to return the retractor system to the collapsed position for removal from the colon.
Figure 28:
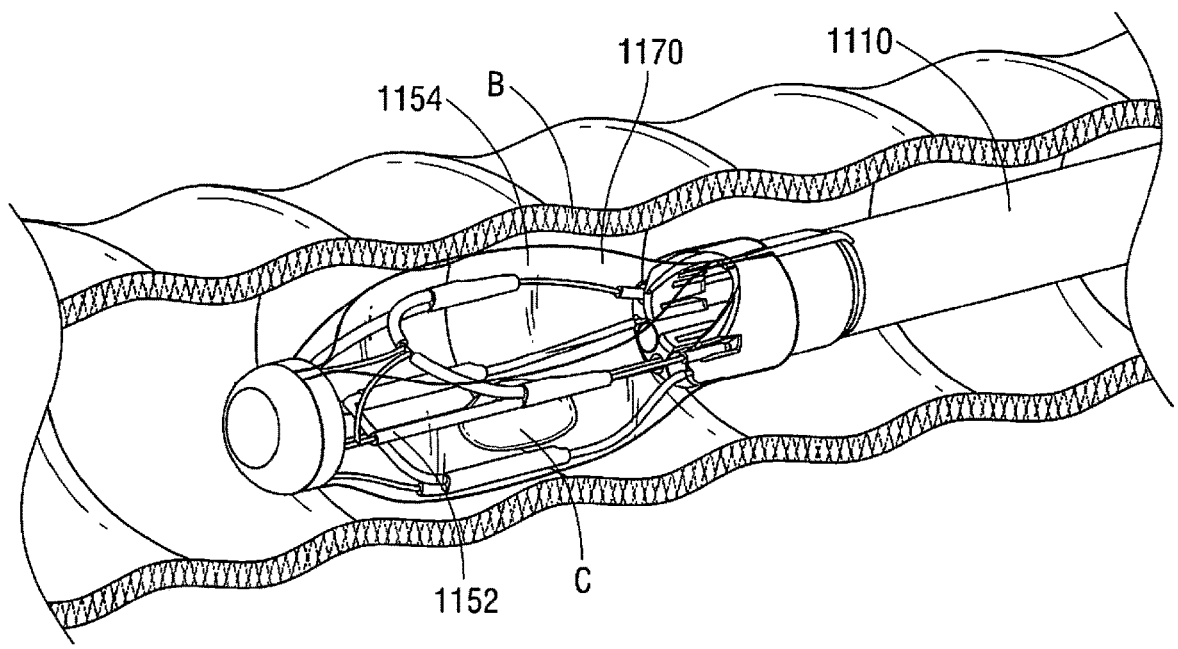
FIG. 28 is a view similar to FIG. 26 showing the retractor system in the collapsed position with the lesion therein.
Figure 29:
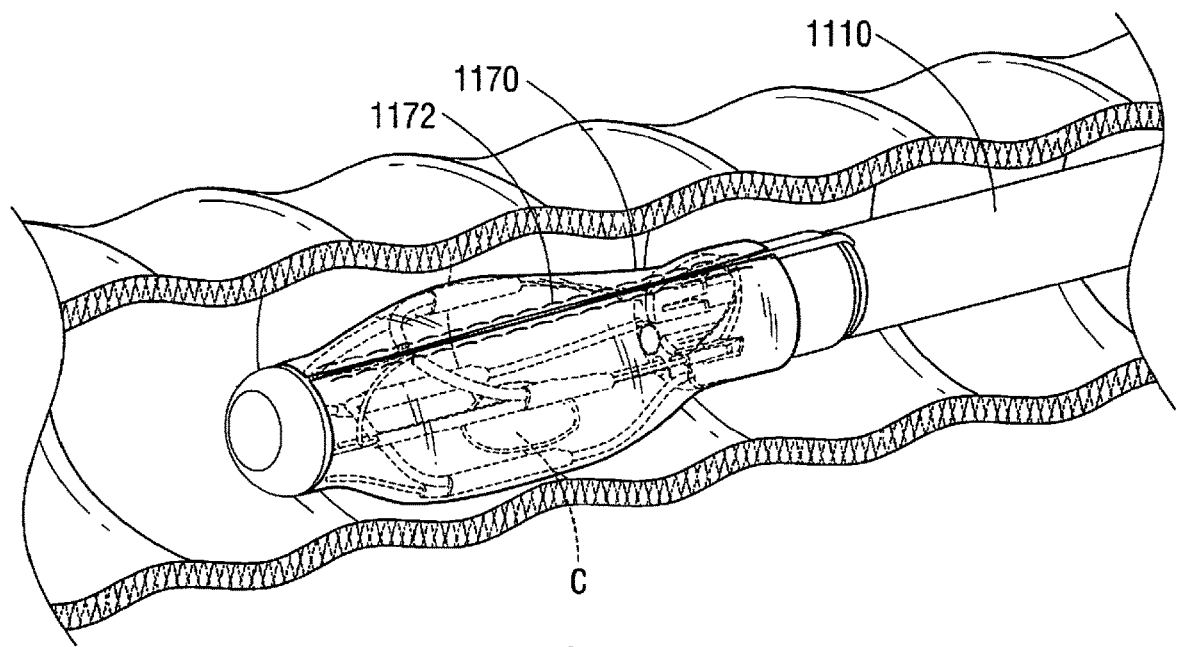
FIG. 29 is a view similar to FIG. 28 showing the covering member closed to encapsulate the lesion for removal.

After removal of the polyp C from the colon wall B, it is placed within the cover 1170 as shown in FIG. 26, ready for removal from the body. Actuator 1134 can be moved proximally to return the retractor system to the more flexible condition if desired. Actuator 1132 is moved proximally in the direction of the arrow of FIG. 27 to return the expanded retractor elements 1152, 1154, 1156 and 1158 to their collapsed position of FIG. 28 for removal of the catheter 1110. The string or suture 1172 is then tensioned to close the cover (bag) 1170 as shown in FIG. 29, forming a bag to encapsulate the polyp C. The switch 1175 can then be moved to the position of FIG. 31B to lock the string 1172 and thereby maintain the cover 1170 in the closed position. Catheter 1110 is then removed from the colon B with the polyp C protected (encapsulated) within the cover 1170. Note that the cover 1170 is preferably transparent so that the drawings illustrate the retractor elements, bridge members, beam, etc. However, to facilitate understanding of the cover 1170, FIG. 29 shows the retractor elements, bridge elements, beam etc. in phantom insider the bag/cover 1170.

Note the endoscopic instruments can be used for partial tissue resection, for example, submucosal or subserosal resection. The endoscopic instruments could also be utilized for full thickness tissue resection. The instruments enable removal of the lesion with healthy tissue margins, thereby providing a complete, en-block removal of the pathological lesion.

One of skill will appreciate that the handle can be any of a variety of shapes to provide a desired or ergonomic position for operation of the system. By way of example, the retractor actuator can be configured as a finger-activated button on the handle that slides back and forth through a slot in the handle to expand or collapse the retractor elements. A means for dynamically adjusting or ratcheting the retractor position can be provided along the handle slot to lock the position of the retractor elements in place when the retractor actuator button is not pressed. A button on the opposite side of the handle can be operatively connected to the stabilizer subsystem to convert the flexible beam into a rigid beam, or convert the rigid beam into a flexible beam. The handle can have inner channels routed axially, for example, within the body of the handle and in communication with ports for tools and endoscope introduction into the outer tube. In some embodiments, the handle can be configured to require that the stabilizer actuator is activated before the retractor actuator can be activated, serving as a "safety" mechanism in the operation of the system.

Without intending to be limited to any theory or mechanism of action, the above teachings were provided to illustrate a sampling of all possible embodiments rather than a listing of the only possible embodiments. As such, it should be appreciated that there are several variations contemplated within the skill in the art that will also fall into the scope of the claims.

What is claimed is:

1. A system comprising:
a flexible catheter having a proximal region and a distal region, a first flexible tube and a second flexible tube;
the first flexible tube having a first channel extending therethrough, the first channel for removably receiving a first endoscopic tool, the first endoscopic tool movable to a curved position beyond the distal region of the flexible catheter, the curved position including a first curved portion extending away from the longitudinal axis thereof, and a second curved portion extending toward the longitudinal axis thereof;
the second flexible tube having a second channel extending therethrough for removably receive a second endoscopic tool, the second endoscopic tool movable to a curved position beyond the distal region of the flexible catheter, the curved position including a first curved portion extending away from the longitudinal axis thereof, and a second curved portion extending toward the longitudinal axis thereof.

2. The system of claim 1, further comprising an endoscope positionable within the flexible catheter, the endoscope movable independently of the first and second endoscopic tools.

3. The system of claim 2, wherein the first endoscopic instrument is extendible through a first lumen of the flexible catheter, the second endoscopic instrument is extendible through a second lumen of the flexible catheter, and the endoscope extends through a third lumen of flexible catheter.

4. The system of claim 3, wherein a proximal end of the flexible catheter includes a first port in communication with the first lumen, and a second port in communication with the second lumen, the first and second endoscopic tools insertable through the first port and the second flexible tube insertable through the second port.

5. The system of claim 1, wherein at least one of the first and second flexible tubes float with respect to the flexible catheter.

6. The system of claim 5, further comprising an endoscope within the flexible catheter, wherein the endoscope floats within the flexible catheter.

7. The system of claim 1, wherein a distal tip of the first endoscopic tool is configured to extend distally beyond a distal opening of the first flexible tube.

8. The system of claim 1, wherein proximal ends of the first and second endoscopic tools are configured to be manipulated by a user to impart at least one of axial and rotatable movement to the respective first and second endoscopic tools.

9. A system, comprising:
a flexible catheter having a proximal region and a distal region, a first flexible tube and a second flexible tube;
the first flexible tube having a first channel for removably receiving a first endoscopic tool therein, a distal portion of the first endoscopic tool movable from a straight configuration to a curved position relative to the longitudinal axis when extended distally beyond the distal region of the flexible catheter;
the second flexible tube having a second channel extending through a longitudinal axis thereof, the second channel configured and dimensioned to removably receive a second endoscopic tool therein, a distal portion of the second endoscopic tool movable from a straight configuration to a curved position relative to the longitudinal axis when extended distally beyond the distal region of the flexible catheter;

wherein the curved position of the first endoscopic tool includes a first bent portion extending away from the longitudinal axis thereof, and a second bent portion extending toward the longitudinal axis thereof; and wherein the curved position of the second endoscopic tool includes a first bent portion extending away from the longitudinal axis thereof, and a second bent portion extending toward the longitudinal axis thereof.

10. The system of claim 9, further comprising an endoscope positionable within the flexible catheter.

11. The system of claim 10, wherein the endoscope extends through a lumen of the flexible catheter.

12. The system of claim 9, wherein at least one of the first and second flexible tubes float with respect to the flexible catheter.

13. The system of claim 12, further comprising an endoscope positionable within the flexible catheter, wherein the endoscope floats within the flexible catheter.

14. The system of claim 9, wherein a proximal end of the flexible catheter includes first and second ports, the first and second endoscopic tools insertable through the first port and the second flexible tube insertable through the second port.

15. The system of claim 9, wherein respective distal tips of the first and second endoscopic tools are extendable distally beyond a distal opening of the first and second flexible tubes.

16. The system of claim 9, wherein proximal ends of the first and second endoscopic tools are configured to be manipulated by a user to impart at least one of axial and rotatable movement to the respective first and second endoscopic tools.

17. A system, comprising:
a flexible catheter having a proximal region and a distal region, a first flexible tube and a second flexible tube, and a reversibly-expandable retractor extending distally beyond a distal end of the flexible catheter;

the first flexible tube having a first channel for removably receive a first endoscopic tool therein;

a distal portion of the first endoscopic tool movable from a straight configuration to a curved position relative to the longitudinal axis when extended distally beyond the distal region of the flexible catheter;

the second flexible tube having a second channel for removably receive a second endoscopic tool therein;

a distal portion of the second endoscopic tool movable from a straight configuration to a curved position relative to the longitudinal axis when extended distally beyond the distal region of the flexible catheter;

wherein the curved position of the first endoscopic tool includes a first bent portion extending away from the longitudinal axis thereof, and a second bent portion extending toward the longitudinal axis thereof; and wherein the curved position of the second endoscopic tool includes a first bent portion extending away from the longitudinal axis thereof, and a second bent portion extending toward the longitudinal axis thereof.

18. The system of claim 17, wherein the retractor includes first and second flexible elements moveable from a collapsed configuration to an expanded configuration.

19. The system of claim 18, wherein respective distal tips of the first and second endoscopic tools are extendable distally beyond a distal opening of the first and second flexible tubes within a working space formed by the first and second elements in the expanded configuration.

20. The system of claim 19, further comprising an endoscope positionable within the flexible catheter, wherein a distal portion of the endoscope is positionable within the working space.

* * * * *